US 12,131,235 B2

(12) United States Patent
Machida et al.

(10) Patent No.: US 12,131,235 B2
(45) Date of Patent: Oct. 29, 2024

(54) MEDICAL INFORMATION PROCESSING APPARATUS, MEDICAL INFORMATION PROCESSING METHOD, AND NON-TRANSITORY COMPUTER-READABLE STORAGE MEDIUM

(71) Applicant: CANON KABUSHIKI KAISHA, Tokyo (JP)

(72) Inventors: Yoshihito Machida, Kanagawa (JP); Yoshinori Hirano, Chiba (JP); Hideaki Miyamoto, Tokyo (JP); Daisuke Yamada, Kanagawa (JP); Akiya Nakayama, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 943 days.

(21) Appl. No.: 17/163,928

(22) Filed: Feb. 1, 2021

(65) Prior Publication Data

US 2021/0158218 A1 May 27, 2021

Related U.S. Application Data

(63) Continuation of application No. PCT/JP2019/023051, filed on Jun. 11, 2019.

(30) Foreign Application Priority Data

Aug. 14, 2018 (JP) ................................ 2018-152719

(51) Int. Cl.
*G06N 20/00* (2019.01)
*G06T 7/00* (2017.01)
(Continued)

(52) U.S. Cl.
CPC ........... *G06N 20/00* (2019.01); *G06T 7/0012* (2013.01); *G16H 30/20* (2018.01); *G16H 30/40* (2018.01); *G06T 2207/20081* (2013.01)

(58) Field of Classification Search
None
See application file for complete search history.

(56) References Cited

U.S. PATENT DOCUMENTS 11,914,918 B2 * 2/2024 Machida ............ G06V 10/7784
2012/0197827 A1 8/2012 Mineno
(Continued)

FOREIGN PATENT DOCUMENTS

JP H04-261649 A 9/1992
JP 2011-059810 A 3/2011
(Continued)

OTHER PUBLICATIONS

US Non Final Office Action dated Aug. 1, 2023, issued in U.S. Appl. No. 17/163,888, pp. 1-44.
(Continued)

*Primary Examiner* — Leon Flores
(74) *Attorney, Agent, or Firm* — Carter, DeLuca & Farrell LLP

(57) ABSTRACT

A medical information processing apparatus comprises: an obtaining unit that obtains medical information; a learning unit that performs machine learning on a function of the medical information processing apparatus using the medical information; an evaluation data holding unit that holds evaluation data for evaluating a learning result of the learning unit; and an evaluating unit that evaluates a learning result obtained through machine learning, based on the evaluation data.

21 Claims, 15 Drawing Sheets

(51) Int. Cl.
*G16H 30/20* (2018.01)
*G16H 30/40* (2018.01)

(56) References Cited

U.S. PATENT DOCUMENTS

| | | |
|---|---|---|
| 2015/0379432 A1 | 12/2015 | Ando |
| 2017/0351972 A1 | 12/2017 | Kaniwa |
| 2018/0150675 A1 | 5/2018 | Kamiyama |
| 2019/0030370 A1* | 1/2019 | Hibbard ............... A61N 5/1067 |
| 2019/0076108 A1 | 3/2019 | Machida |
| 2019/0192880 A1* | 6/2019 | Hibbard ................ G16H 30/20 |
| 2020/0236303 A1 | 7/2020 | Machida |

FOREIGN PATENT DOCUMENTS

| | | |
|---|---|---|
| JP | 2011-212094 A | 10/2011 |
| JP | 2012-159886 A | 8/2012 |
| JP | 2016-198197 A | 12/2016 |
| JP | 2017-185007 A | 10/2017 |
| JP | 2017-215828 A | 12/2017 |
| WO | 2014/155690 A1 | 10/2014 |
| WO | 2017/017722 A1 | 2/2017 |
| WO | 2018/070285 A1 | 4/2018 |
| WO | 2018/120426 A1 | 7/2018 |
| WO | 2019/150813 A1 | 8/2019 |

OTHER PUBLICATIONS

International Search Report issued in International Application No. PCT/JP2019/023051 dated Sep. 17, 2019, pp. 1, English Translation.

Ishii, T., et al., "Analysis on generic object recognition technique using Conventional Neural Network" Information Processing Society of Japan Technical Report (May 2014) pp. 1-8, vol. 2014-CVIM-192 No. 14.

Yanase, M., et al., "Proposal of Visual Recognition System based on Machine Learning Method" The Papers of Technical Meeting on Information Oriented Industrial System, IEE Japan (May 2014) pp. 1-8.

Notice of Reasons for Refusal issued in corresponding JP Patent Application No. 2018-152719, dated Oct. 3, 2022, pp. 1-6, with English translation.

Notice of Reasons for Refusal issued in corresponding JP Patent Application No. 2018-152719, dated Apr. 3, 2023, pp. 1-10, with English translation.

Morita, M., "Simultaneous Segmentation of Multiple Organs Using Data Items of First Layer, Information Processing" Information Processing Society of Japan, IPSJ SIG Technical Report (May 2014) vol. 2014-CVIM-192, No. 16, with English abstract.

* cited by examiner

|  | RECOGNIZE IMAGE | IMAGE PROCESSING | PHOTOGRAPHIC FAILURE RECOGNITION | IMAGING SITE |
|---|---|---|---|---|
| EVALUATION DATA 1 | ○ | × | × | CHEST |
| EVALUATION DATA 2 | × | ○ | × | CHEST |
| EVALUATION DATA 3 | × | × | ○ | ABDOMEN |
| EVALUATION DATA 4 | ○ | ○ | × | ABDOMEN |
| EVALUATION DATA 5 | ○ | × | ○ | CHEST |
| EVALUATION DATA 6 | ○ | ○ | × | HEAD |
| EVALUATION DATA 7 | ○ | ○ | ○ | CHEST |

FIG. 7B

|  | FUNCTION | IMAGING SITE | EVALUATION DATA |
|---|---|---|---|
| LEARNING RESULT 1 | RECOGNIZE IMAGE | CHEST | EVALUATION DATA 1<br>EVALUATION DATA 5<br>EVALUATION DATA 7 |
| LEARNING RESULT 2 | IMAGE PROCESSING | ABDOMEN | EVALUATION DATA 4 |
| LEARNING RESULT 3 | PHOTOGRAPHIC FAILURE RECOGNITION | HEAD | EVALUATION DATA 3<br>EVALUATION DATA 5<br>EVALUATION DATA 7 |
| LEARNING RESULT 4 | OPERATION RECOGNITION | CHEST | NONE |

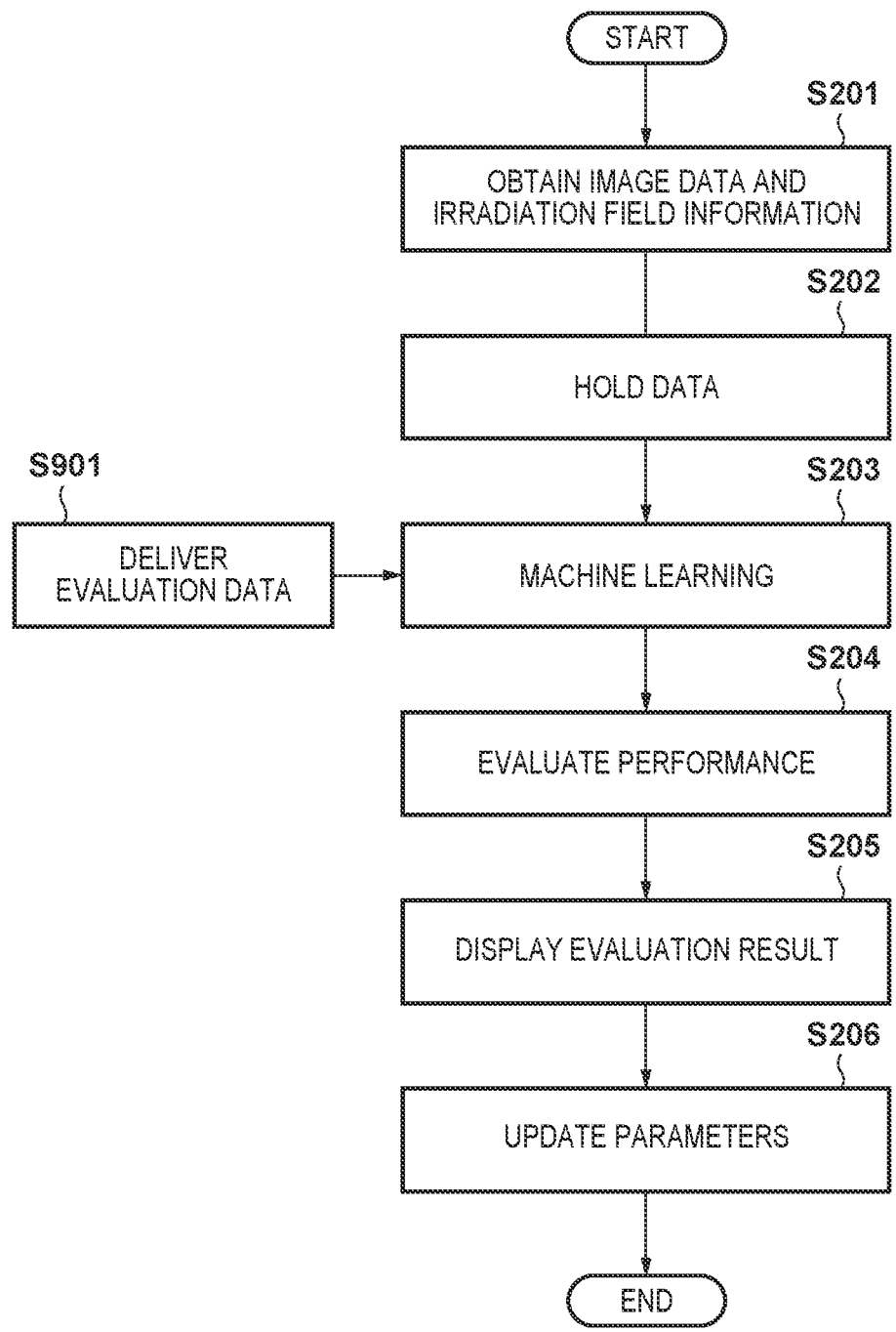

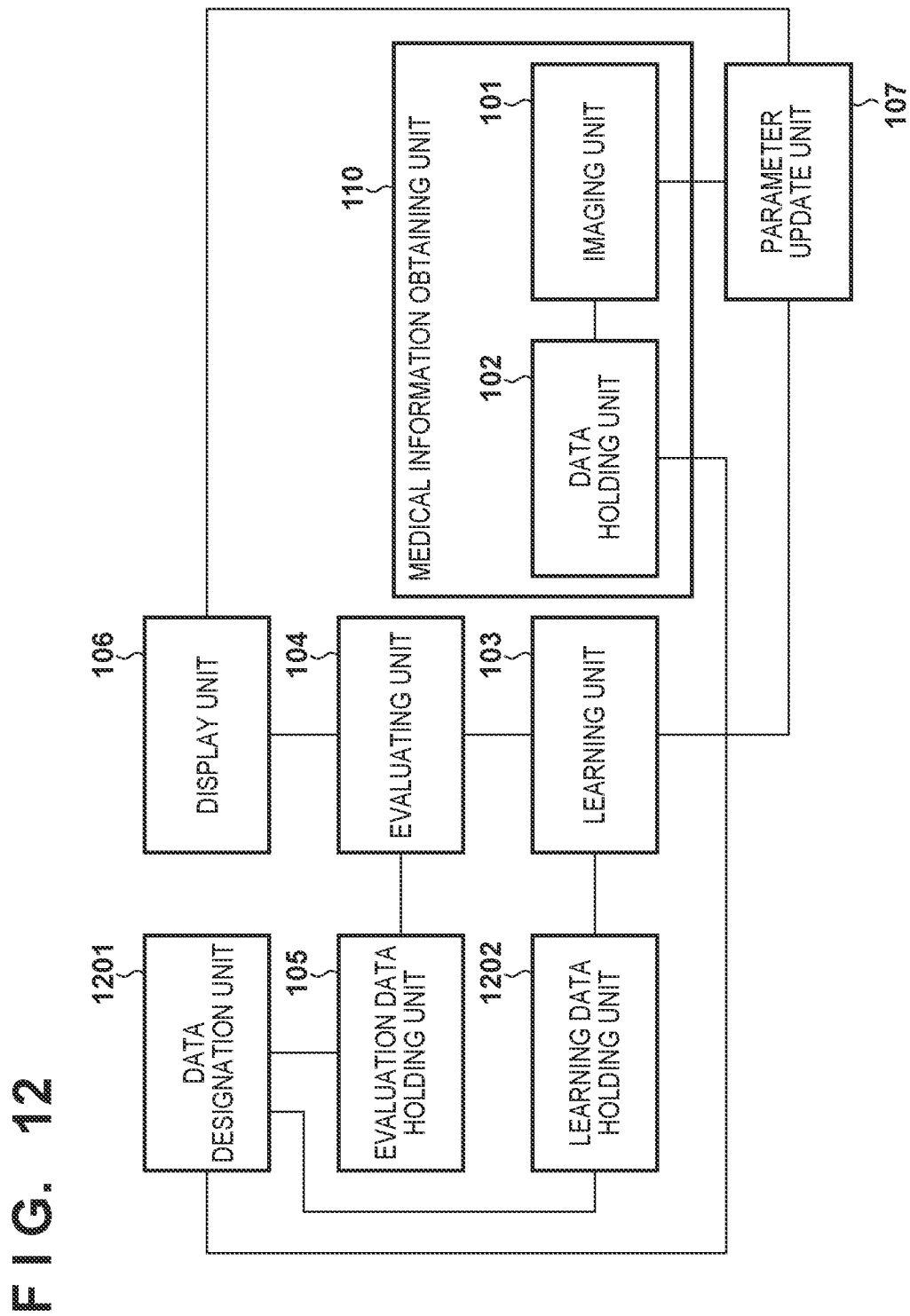

MEDICAL INFORMATION PROCESSING APPARATUS, MEDICAL INFORMATION PROCESSING METHOD, AND NON-TRANSITORY COMPUTER-READABLE STORAGE MEDIUM

CROSS-REFERENCE TO RELATED APPLICATIONS

This application is a Continuation of International Patent Application No. PCT/JP2019/023051, filed Jun. 11, 2019, which claims the benefit of Japanese Patent Application No. 2018-152719, filed Aug. 14, 2018, both of which are hereby incorporated by reference herein in their entirety.

BACKGROUND OF THE INVENTION

Field of the Invention

The present invention relates to a medical information processing apparatus, a medical information processing method, and non-transitory computer-readable storage medium.

Background Art

A function of providing information that suits user's tendency and taste using machine learning, a function of improving the image analysis accuracy, and the like, in medical information processing apparatuses, have been suggested. Patent Document 1 describes a method for improving the image recognition accuracy through machine learning, and detecting a target object. Also, Patent Document 2 describes a method for recognizing a division pattern, an irradiation field, an imaging posture, and an imaging part of a radiation image, using a neural network.

CITATION LIST

Patent Literature

PTL1: Japanese Patent Laid-Open No. 2017-185007
PTL2: Japanese Patent Laid-Open No. H04-261649

Non Patent Literature

NPL 1: Analysis on generic object recognition technique using Conventional Neural Network, Information Processing Society of Japan Technical Report Vol. 2014-CVIM-192 No. 14 (to be referenced in embodiments)

There has been no suggestion on validity examination for examining whether or not performance required for achieving an intended use, which is a user's clinical request, is me when performance is changed using the above-described machine learning, nor maintenance of the reliability of data for performing the above validity examination.

SUMMARY OF THE INVENTION

According to one mode of the present invention, a technique for enabling validity examination of machine learning in a medical information processing apparatus is provided.

According to one aspect of the present invention, there is provided a medical information processing apparatus, comprising: an obtaining unit configured to obtain medical information; a learning unit configured to perform machine learning on a function of the medical information processing apparatus using the medical information; an evaluation data holding unit configured to hold evaluation data in which a correct answer to be obtained by executing the function is known, the evaluation data being for evaluating a learning result of the learning unit; and an evaluating unit configured to evaluate a learning result obtained through machine learning, based on the evaluation data.

Further features of the present invention will become apparent from the following description of exemplary embodiments with reference to the attached drawings.

BRIEF DESCRIPTION OF THE DRAWINGS

FIG. 5 is a diagram showing an example of the difference between a correct answer for an irradiation field and a result obtained through learning.

FIG. 7A is a diagram showing an example of attached information of image data according to Modification 2.

FIG. 7B is a diagram showing an example of attached information of image data according to Modification 2.

FIG. 9 is a flowchart showing the processing procedure of the medical information processing apparatus according to the second embodiment.

FIG. 12 is a diagram showing an exemplary function configuration of a medical information processing apparatus according to a third embodiment.

DESCRIPTION OF THE EMBODIMENTS

Embodiments of the present invention will be described below with reference to the accompanying drawings. Note that, in the embodiments, a medical information processing apparatus for a radiation image will be described, but the present invention is also applicable to medical information processing apparatuses that use another modality, such as CT apparatuses, MRI apparatuses, ultrasonic apparatuses, fundus cameras, OCTs, and endoscopes. The present invention is also applicable to a medical information processing apparatus that uses a plurality of types of modalities. Note that, in the embodiments below, the term "radiation" may include α-rays, β-rays, γ-rays, particle beams, cosmic rays, and the like in addition to X-rays.

First Embodiment

Figure 1:
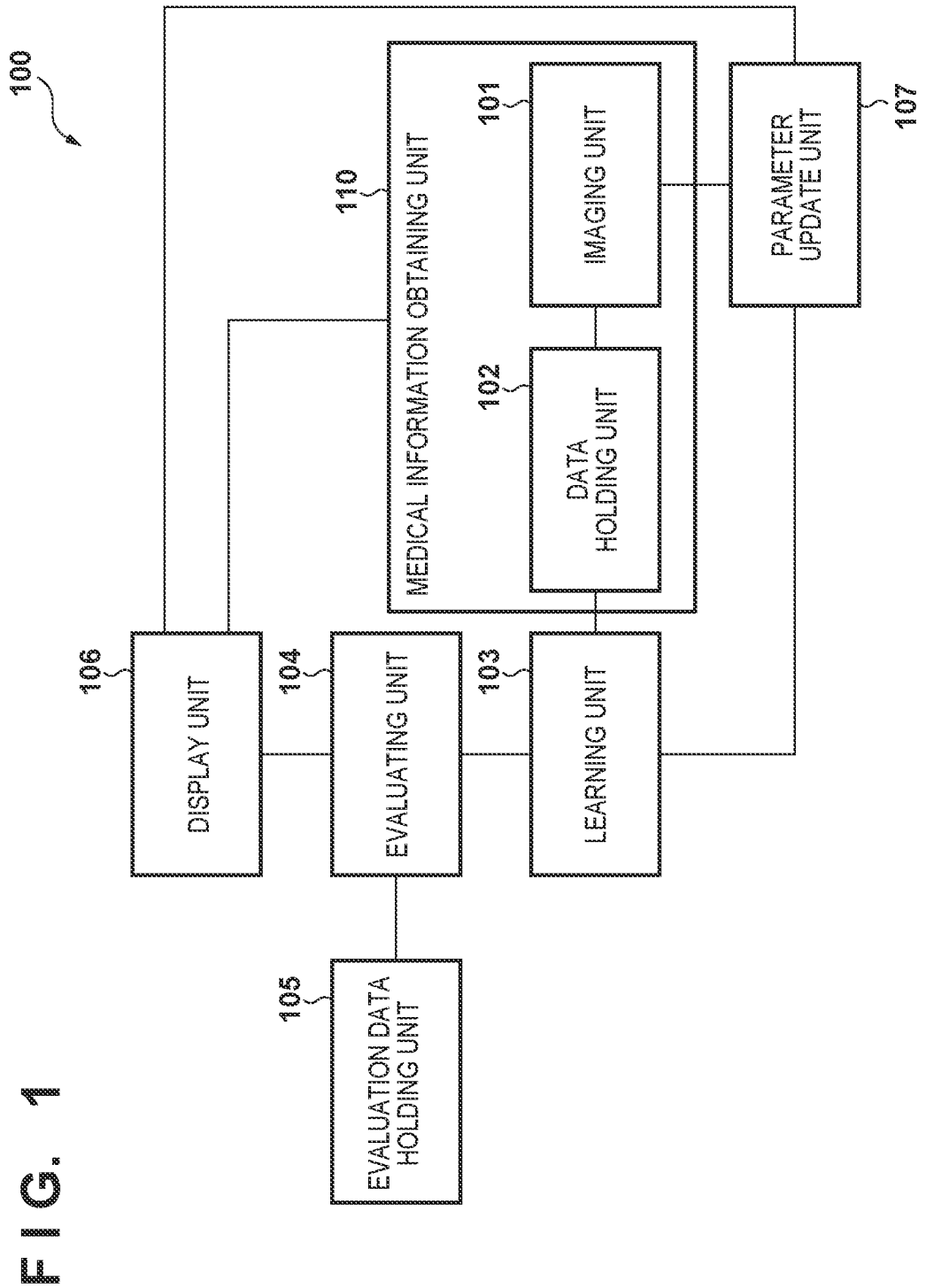
FIG. 1 is a diagram showing an exemplary function configuration of a medical information processing apparatus according to a first embodiment.

FIG. 1 is a block diagram showing an exemplary function configuration of a medical information processing apparatus according to a first embodiment. In a medical information processing apparatus 100, a medical information obtaining unit 110 obtains medical information. A learning unit 103 performs machine learning for a function of the medical information processing apparatus, using the obtained medical information. An evaluation data holding unit 105 holds evaluation data for evaluating a result of learning performed by the learning unit 103, namely evaluation data in which a correct answer to be obtained by executing the function is known. An evaluating unit 104 evaluates the learning result (learning state) obtained through machine learning performed by the learning unit 103, based on the evaluation data. A display unit 106 displays the evaluation result for the learning result. A parameter update unit 107 updates parameter used by the above function of the medical information processing apparatus, based on the evaluation performed by the evaluating unit 104.

In the medical information obtaining unit 110, an imaging unit 101 obtains a medical image to be used as medical information. Examples of the medical image include a radiation image, a CT image, an MRI image, an ultrasonic image, an eye-fundus image, an OCT image, and an endoscope image. In addition, the medical information may include information attached to the medical image (e.g., a tube voltage, an imaging part). The medical information obtaining unit 110 obtains medical information that includes a medical image and information attached to the medical image (hereinafter, attached information), and stores the medical information in a data holding unit 102.

The medical information processing apparatus 100 has a function of image recognition, image processing, diagnosis support, or the like that uses a medical image. When the learning unit 103 performs learning for the function of the medical information processing apparatus 100, the function (the quality of the function) of the medical information processing apparatus 100 changes. For example, if the learning unit 103 performs learning for image recognition that uses a medical image, the accuracy of image recognition changes, if the learning unit 103 performs learning for image processing, the accuracy of image processing changes, or, if the learning unit 103 performs learning for diagnosis support, the accuracy of diagnosis support changes.

The evaluation data holding unit 105 holds evaluation data corresponding to the function of the medical information processing apparatus 100. The evaluation data includes, for example, a medical image and correct-answer data corresponding to each type of learning (image recognition, image processing, diagnosis support, or the like). Specifically, evaluation data is defined as a medical image and correct-answer data that is known in correspondence with the medical image. For example, evaluation data related to learning for image recognition that uses a medical image includes a medical image and region information (an irradiation field, an anatomical region, a lesion region, and the like). In addition, for example, evaluation data related to learning for image processing includes a medical image and image processing conditions (a tone processing condition, a noise processing condition, and the like). In addition, for example, evaluation data related to learning for diagnosis support includes a medical image and lesion position information.

In addition, the evaluation data holding unit 105 may hold evaluation data according to image-capturing mode such as an imaging part, an imaging technique and the like. For example, the evaluation data holding unit 105 can divide evaluation data to be processed, according to imaging part such as a chest, an abdomen, a head, and four extremities, and hold the evaluation data. For example, the evaluation data holding unit 105 can hold a medical image that is evaluation data and image processing conditions (e.g., a tone processing condition and a noise processing condition) according to imaging part. In addition, for example, the evaluation data holding unit 105 can distinguish evaluation data according to imaging technique such as moving image shooting and still image shooting, and hold the evaluation data. For example, the evaluation data holding unit 105 can hold a medical image that is evaluation data and image processing conditions (e.g., a tone processing condition and a noise processing condition) according to imaging technique.

The evaluating unit 104 analyzes content learned by the learning unit 103 (function of the medical information processing apparatus), reads evaluation data related to the learned content from the evaluation data holding unit 105, and evaluates the learning result. The evaluating unit 104 processes data to be processed included in the evaluation data based on the function in the system using the learning result of the teaming unit 103, compares the result with correct-answer data included in the evaluation data, and evaluates the learning result. For example, when evaluating teaming for image recognition that uses a medical image, the evaluating unit 104 reads, from the evaluation data holding unit 105, evaluation data related to learning for image recognition that uses a medical image, and evaluates the learning result related to image recognition. In addition, for example, when evaluating learning for image processing that uses a medical image is evaluated, the evaluating unit 104 reads, from the evaluation data holding unit 105, evaluation data related to learning for image processing that uses a medical image, and evaluates the learning result related to image processing. In addition, for example, when evaluating learning for diagnosis support that uses a medical image, the evaluating unit 104 reads, from the evaluation data holding unit 105, evaluation data related to learning for diagnosis support, and evaluates the learning result related to diagnosis support.

Note that, in the above description, evaluation data to be used is selected in accordance with the type of function (type of learning for image recognition, image processing, or diagnosis support), but there is no limitation thereto. For example, a configuration may also be adopted in which the evaluating unit 104 reads evaluation data related to the image-capturing mode when the medical image was obtained, in accordance with image-capturing mode that is based on medical information learned by the learning unit 103, and evaluates the learning result. Examples of the image-capturing mode include imaging parts such as a chest, abdomen, a head, and four extremities as described above. More specifically, when learning for image recognition that uses a medical image of a, chest is evaluated, the evaluating unit 104 reads evaluation data from a medical image of a chest, and evaluates the learning result related to image recognition.

The display unit 106 displays the evaluation result for the learning result. The display unit 106 can also display a medical image. The display unit 106 can display whether the learning result of machine learning (e.g., the accuracy of image recognition, the accuracy of image processing, or the accuracy of diagnosis support) has improved or deteriorated. The parameter update unit 107 updates a parameter that is used by the function of the medical information processing apparatus, based on evaluation performed by the evaluating unit 104. For example, when the learning result of machine learning performed by the learning unit 103 (e.g., the accuracy of image recognition, the accuracy of image processing, or the accuracy of diagnosis support) improves, the parameter update unit 107 updates the parameter of the function of the medical information processing apparatus.

Figure 15:
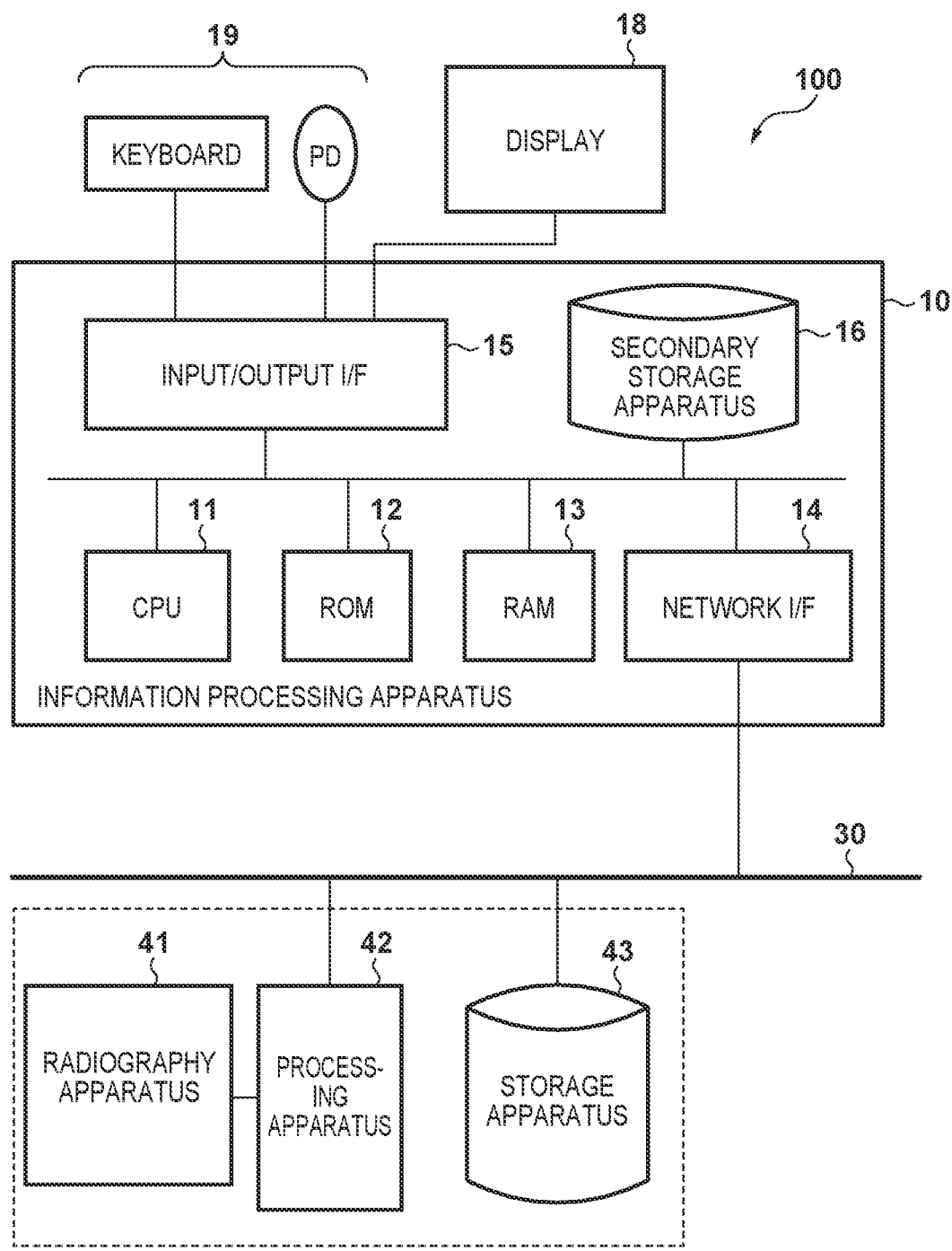
FIG. 15 is a block diagram showing an exemplary hardware configuration of a medical information system according to an embodiment of the present invention.

FIG. 15 is a block diagram showing an exemplary hardware configuration of the medical information processing apparatus 100 that realizes the above function units.

A radiography apparatus 41 detects radiation emitted from a radiation generation unit (not illustrated), and obtains a radiation image as a medical image. A processing apparatus 42 performs image recognition, image processing, diagnosis support, and the like based on the radiation image obtained by the radiography apparatus 41. A storage apparatus 43 stores a radiation image obtained by the radiography apparatus 41 and attached information of the image, and the radiation image processed by the processing apparatus 42. The processing apparatus 42 and the storage apparatus 43 are connected to a network 30. Note that, the processing apparatus 42 does not need to be an independent apparatus, and, for example, the processing apparatus 42 may also be included in an information processing apparatus 10, or may also be included in the radiography apparatus 41.

In addition, the information processing apparatus 10 is connected to the network 30. In the information processing apparatus 10, a CPU 11 controls the information processing apparatus 10 by executing a program stored in a ROM 12 or a RAM 13. The ROM 12 is a read-only non-volatile memory, and the RAM 13 is an all-time read/write volatile memory. A network I/F 14 connects the information processing apparatus 10 and the network 30. An input/output I/F 15 connects a display 18 and an operation apparatus 19 such as a keyboard and pointing device to the information processing apparatus 10. A secondary storage apparatus 16 is constituted by a hard disk and the like, and stores various types of data and programs. A bus 17 communicably connects the above units.

In the above configuration, for example, the imaging unit 101 can be realized by the radiography apparatus 41 and the processing apparatus 42. Also, the learning unit 103, the evaluating unit 104, the display unit 106, and the parameter update unit 107 can be realized by the CPU 11 executing a predetermined program stored in the ROM 12 or the RAM 13, in the information processing apparatus 10. In addition, the data holding unit 102 may be realized by the processing apparatus 42 using the storage apparatus 43, and the evaluation data holding unit 105 may be realized by the information processing apparatus 10 using the storage apparatus 43.

An example will be described below in which machine learning for improving the accuracy of the function of irradiation field recognition in a radiation image is applied to the medical information processing apparatus 100 according to the first embodiment that has above-described configuration. The imaging unit 101 has a function of detecting radiation that has passed through a subject, and generating a radiation image (the radiography apparatus 41), and an irradiation field recognition function of specifying an irradiation field region from a captured radiation image (the processing apparatus 42).

Figure 2:
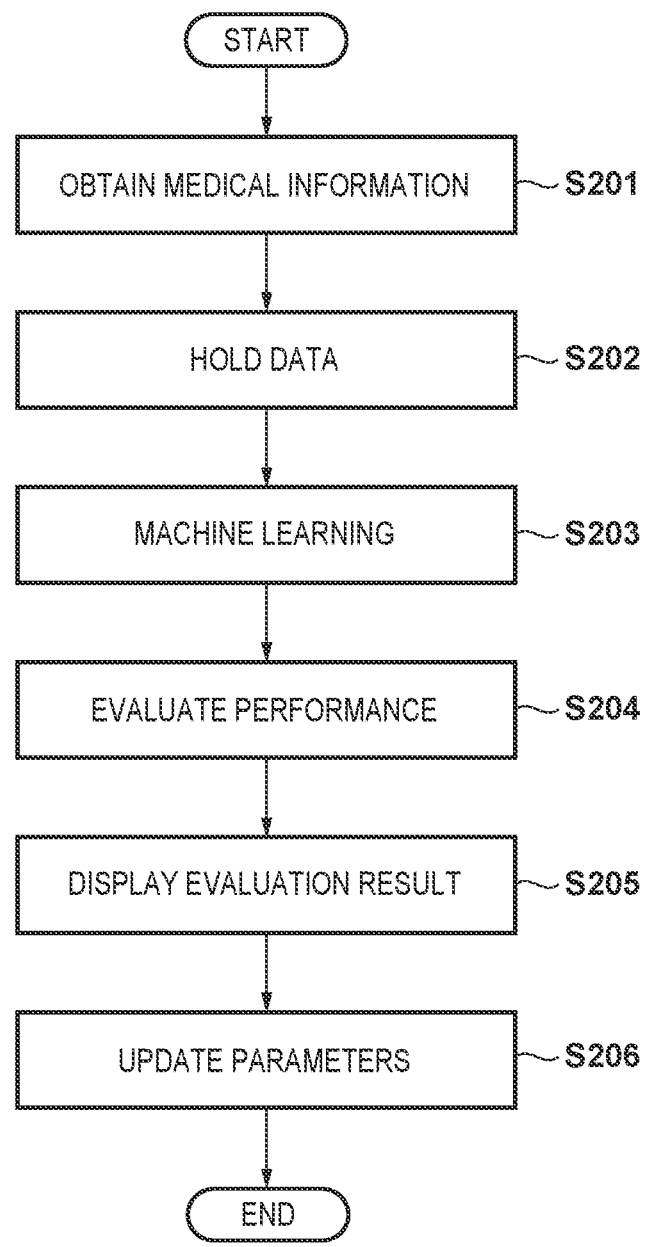
FIG. 2 is a flowchart showing the processing procedure of the medical information processing apparatus according to the first embodiment.

Processing that is performed by the medical information processing apparatus 100 will be described with reference to FIG. 2. FIG. 2 is a flowchart illustrating processing of the medical information processing apparatus 100 according to the first embodiment. In step S201, the imaging unit 101 obtains a radiation image through imaging that uses radiation, and obtains irradiation field information indicating the irradiation field in the radiation image. The irradiation field information is information regarding an irradiated region in a radiation image. The irradiation field information is data in which each coordinate of an irradiation field in a radiation image is set to 0, and each coordinate out of the irradiation field is set to 1, for example. The irradiation field refers to a region in which radiation has reached the imaging unit 101, and a region outside of the irradiation field is a region in which radiation has not reached the imaging unit 101, and that excludes the irradiation field, Reference numeral 501 in FIG. 5 indicates an example of the irradiation field information. The irradiation field information is obtained as a result of the user designating a region or as a result of the user confirming irradiation field information obtained using the irradiation field recognition function (the processing apparatus 42) of the medical information processing apparatus 100, and correcting the irradiation field region as necessary. An algorithm that uses a learning result of a machine learning algorithm is used for the irradiation field recognition function.

in step S202, the data holding unit 102 holds, as medical information, the radiation image and irradiation field information obtained in step S201. In other words, the data holding unit 102 holds a radiation image captured by the imaging unit 101 and information regarding the irradiated region in the radiation image (irradiation field information).

In step S203, the learning unit 103 performs machine learning related to the irradiation field recognition function, using the radiation image and irradiation field information in the data holding unit 102, and obtains a learning result. For example, a Convolution Neural Network (hereinafter, "CNN") described in NPL 1 can be used for machine learning according to this embodiment. Note that the CNN is exemplary, and there is no limitation thereto. For example, the learning unit 103 can use deep learning such as Recurrent Neural Network or Long Short-Term Memory and machine learning such as Support vector Machine or Ada-Boost. In addition, a learning result according to this embodiment is represented by parameters such as weights or the like of the layers of the CNN, but the learning result is not limited thereto. For example, a configuration may also be adopted in which a layer configuration or the like is obtained as a learning result.

Figure 3:
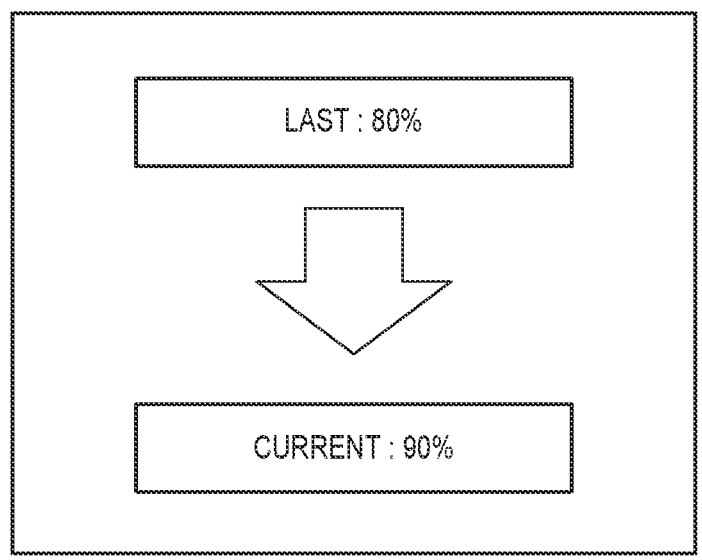
FIG. 3 is a diagram showing a display example of an evaluation result according to the first embodiment.

In step S204, the evaluating unit 104 evaluates the learning result output by the learning unit 103, using evaluation data held in the evaluation data holding unit 105, and obtains an evaluation result. In this embodiment, evaluation data is constituted by a radiation image prepared in advance and irradiation field information thereof (correct-answer data). Note that the evaluation method that is performed by the evaluating unit 104 will be described in detail later. In step S205, the display unit 106 displays the evaluation result obtained by the evaluating unit 104, on a display device. FIG. 3 shows a display example of an evaluation result displayed by the display unit 106. FIG. 3 indicates that the accuracy of irradiation field recognition that is performed using the irradiation field recognition function has improved from 80% to 90%. In other words, the display unit 106 can display whether a learning result of machine learning (the accuracy of irradiation field recognition) has improved or deteriorated.

in step S206, if it is determined that the learning result is valid, based on the evaluation result of the evaluating unit 104, the parameter update unit 107 updates the parameter of the irradiation field recognition function of the imaging unit 101 using the latest learning result. In this manner, if the learning result of machine learning (the accuracy of irradiation field recognition) improves, the parameter update unit 107 updates the parameter of the function of the medical information processing apparatus (the irradiation field recognition function of the imaging unit 101). In other words, if the learning result of machine learning (the accuracy of irradiation field recognition) radiation field deteriorates, the parameter update unit 107 does not update the parameter of the function of the medical information processing apparatus (the irradiation field recognition function of the imaging unit 101). Note that a configuration may also be adopted in which the user determines the validity of the learning result based on the evaluation result such as that shown in FIG. 3, and gives an instruction on whether or not to update the parameter. In this case, the parameter update unit 107 updates the parameter in accordance with a user's instruction.

As a result of performing the processes in steps S201 to S206 as described above, the validity of machine learning can be examined. In addition, in a situation where the function of the medical information processing apparatus may change due to machine learning, an evaluation result after the change is presented to the user, and can be used as a guide when the user makes a determination on the validity. It is possible to examine whether or not performance required for achieving an intended use that is a clinical request is satisfied.

Next, the evaluation processing that is performed by the evaluating unit 104 according to the first embodiment will be described in detail with reference to FIGS. 4A and 4B. According to the first embodiment, the validity of a learning result is evaluated using evaluation data that includes a plurality of pairs of image data (radiation images) and irradiation field information of the image data.

Figure 4A:
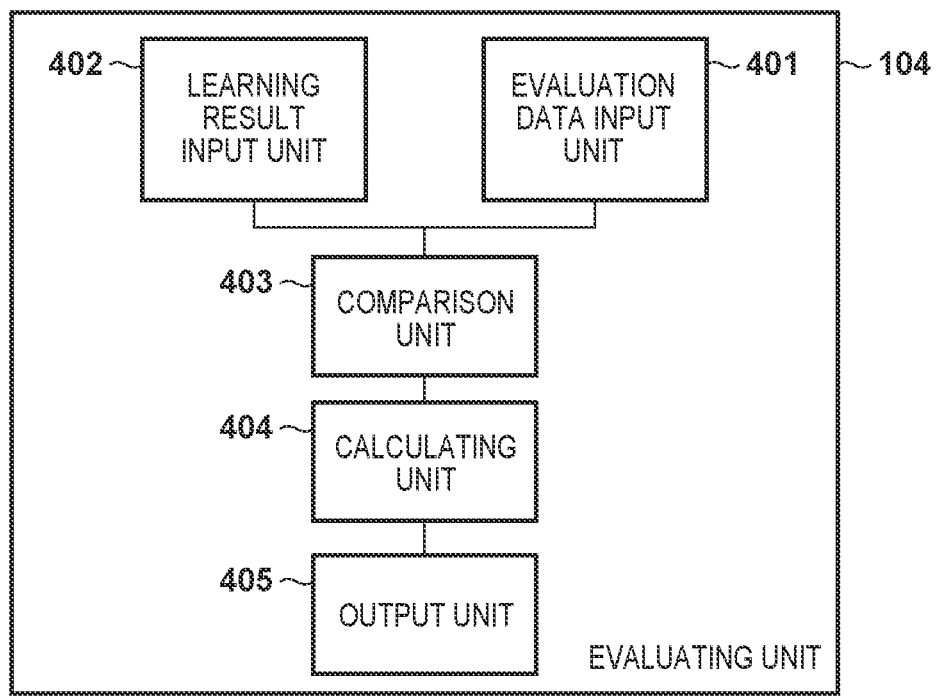
FIG. 4A is a diagram showing an exemplary function configuration of an evaluating unit according to the first embodiment.
Figure 4B:
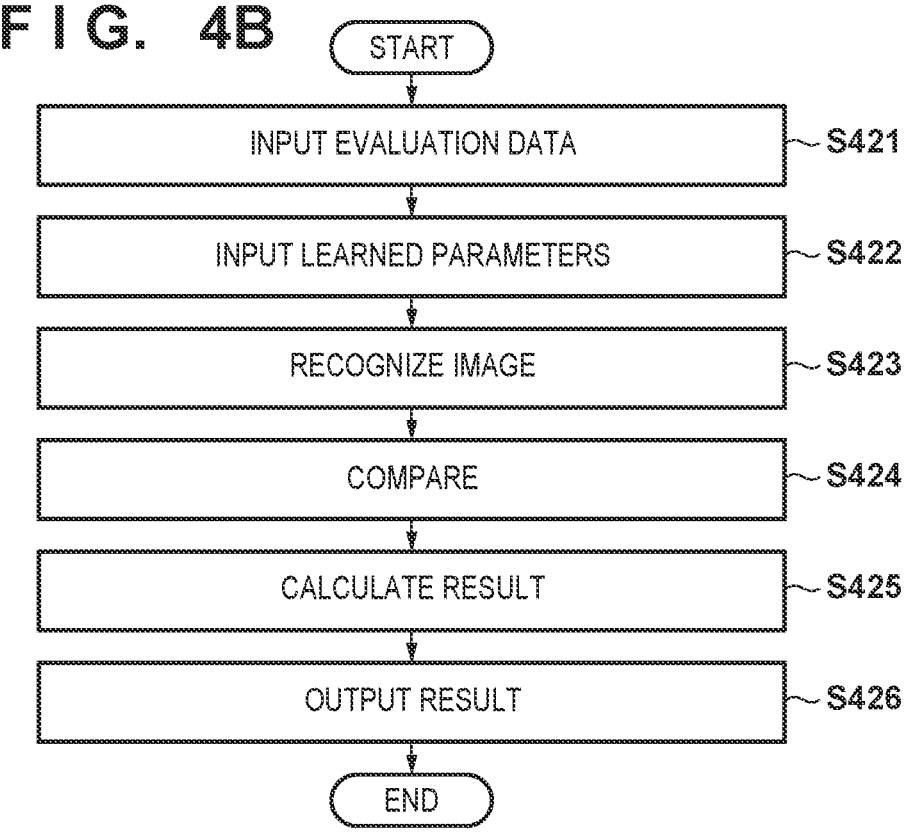
FIG. 4B is a flowchart showing the processing procedure of the evaluating unit according to the first embodiment.

FIG. 4A is a block diagram showing an exemplary function configuration of the evaluating unit 104 according to the first embodiment. In the evaluating unit 104, evaluation data is input to an evaluation data input unit 401 from the evaluation data holding unit 105. Learned parameters, which represent a learning result, are input to a learning result input unit 402 from the learning unit 103. A comparison unit 403 compares correct-answer data in the evaluation data with a result obtained by processing the medical image in the evaluation data using the learned parameters. A calculating unit 404 calculates the match rate between the correct-answer data in the evaluation data and the learned data of the learning result. An output unit 405 outputs the result of the calculation performed by the calculating unit 404.

Next, a flow of processing that is executed by the evaluating unit 104 that has the above configuration will be described in detail with reference to FIG. 4B. In step S421, evaluation data is input to the evaluation data input unit 401 from the evaluation data holding unit 105. As described above, according to this embodiment, evaluation data includes image data serving as a medical image and irradiation field information serving as correct-answer data (hereinafter, "correct-answer irradiation field"). In step S422, the learned parameters representing a learning result of the learning unit 103 are input to the learning result input unit 402. As described above, according to this embodiment, the parameters are weight coefficients of the layers of the CNN. In step S423, the processing apparatus 42 performs image recognition of the image data included in the evaluation data, based on the learned parameters. According to this embodiment, the processing result is represented by irradiation field information (hereinafter, "learned irradiation field"). In step S424, the comparison unit 403 compares the correct-answer irradiation field with the learned irradiation field, and calculates a match rate.

Figure 5:
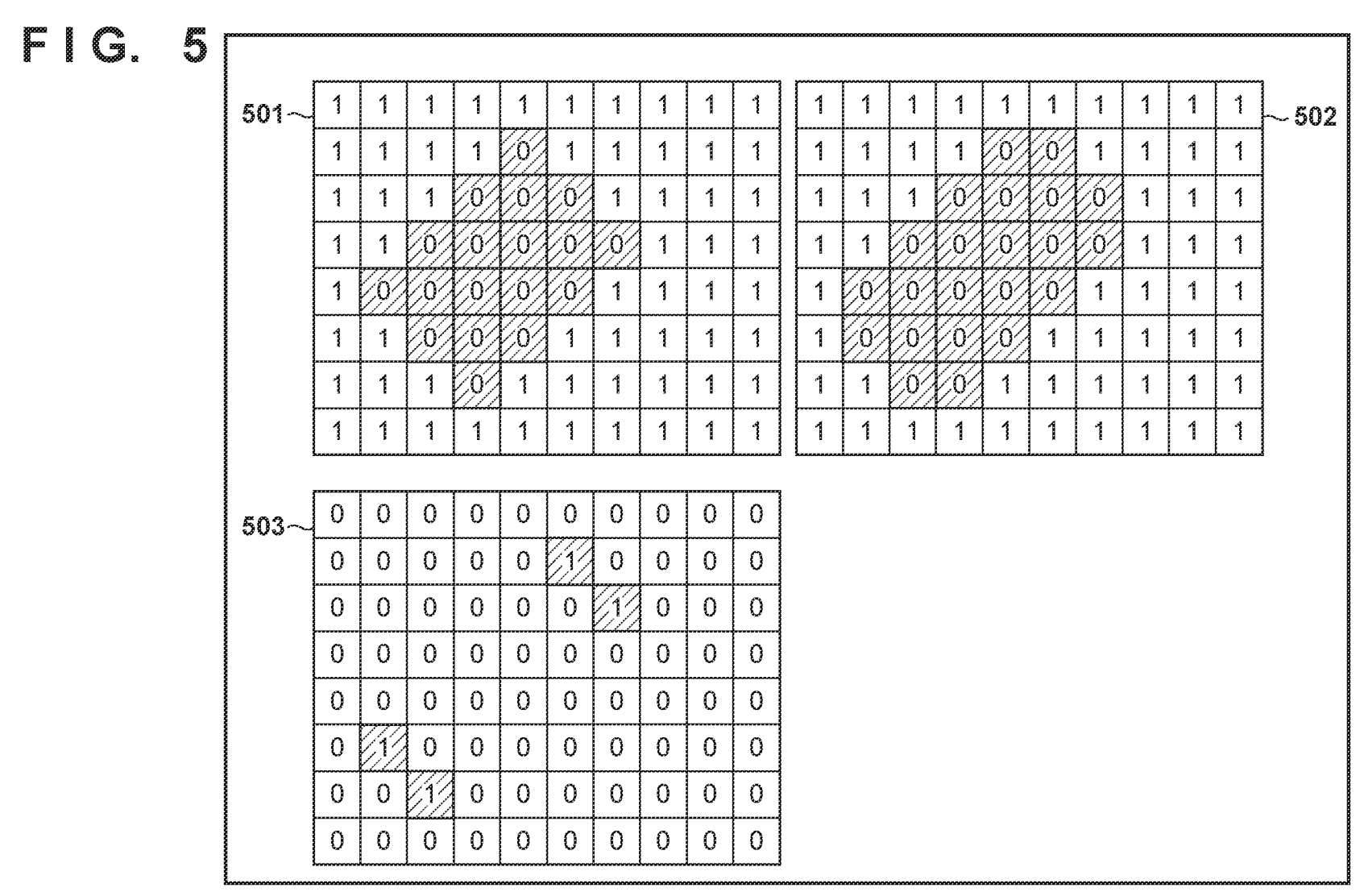

FIG. 5 shows a comparative example of irradiation fields obtained by the comparison unit 403. FIG. 5 shows examples of a correct-answer irradiation field 501, a learned irradiation field 502, and a comparison irradiation field 503. Regarding the correct-answer irradiation field 501 and the learned irradiation field 502, the pixels indicated by "1" are outside of the irradiation field, and pixels indicated by "0" are within the irradiation field. In addition, regarding the comparison irradiation field 503, "0" indicates a pixel in which the correct-answer irradiation field and the learned irradiation field match, and "1" indicates a pixel for which the correct-answer irradiation field and the learned irradiation field do not match. In the example in FIG. 5, 76 pixels out of all of the 80 pixels match, and the match rate in this case is 76/80×100=95%.

In step S425, the calculating unit 404 calculates a result based on all of the comparison results. According to this embodiment, a threshold is provided for the match rate, and recognition accuracy is calculated for all of the comparison results based on a match rate of 95% or higher indicating a correct answer and a match rate of less than 95% indicating a non-correct answer. For example, if 90 examples out of 100 have a match rate of 95% or higher, the recognition accuracy is 90/100×100=90%. In step S426, the output unit 405 outputs the result calculated by the calculating unit 404 to the display unit 106. The user can easily confirm the validity of the learning result updated through machine learning, as a result of the processes in steps S421 to S426 being performed in this manner.

Note that, according to this embodiment, the irradiation field recognition function has been described as an example, but the present invention is applicable to any medical information processing apparatus that uses a machine learning system such as a function of recognizing a region of interest or an imaging part or a function of providing diagnosis support information such as the position and/or the degree of malignancy of a tumor mass. In addition, according to this embodiment, a combination of image data and irradiation field information is used as learning data or evaluation data, but there is no limitation thereto. The present invention is also applicable to any machine learning system that uses, as data, one of image data, diagnostic information, gene information, inspection information of a plurality of modalities, gender, age, and body height, for example.

In addition, in this embodiment, a description has been given on performing machine learning using data obtained by the medical information processing apparatus, but the present invention is also applicable regardless of what system obtained data for performing machine learning. The present invention is also applicable to a medical information processing apparatus that uses a dataset for machine learning that is called public dataset and is publicized on the Internet, for example. In addition, in this embodiment, all of the constituent elements of the medical information processing apparatus 100 do not need to be in the same facility. For example, the medical information processing apparatus may have a configuration in which the imaging unit 101 and the display unit 106 that displays a validity evaluation result are in a hospital, and the other constituent elements are in a cloud.

Modification 1

Figure 6:
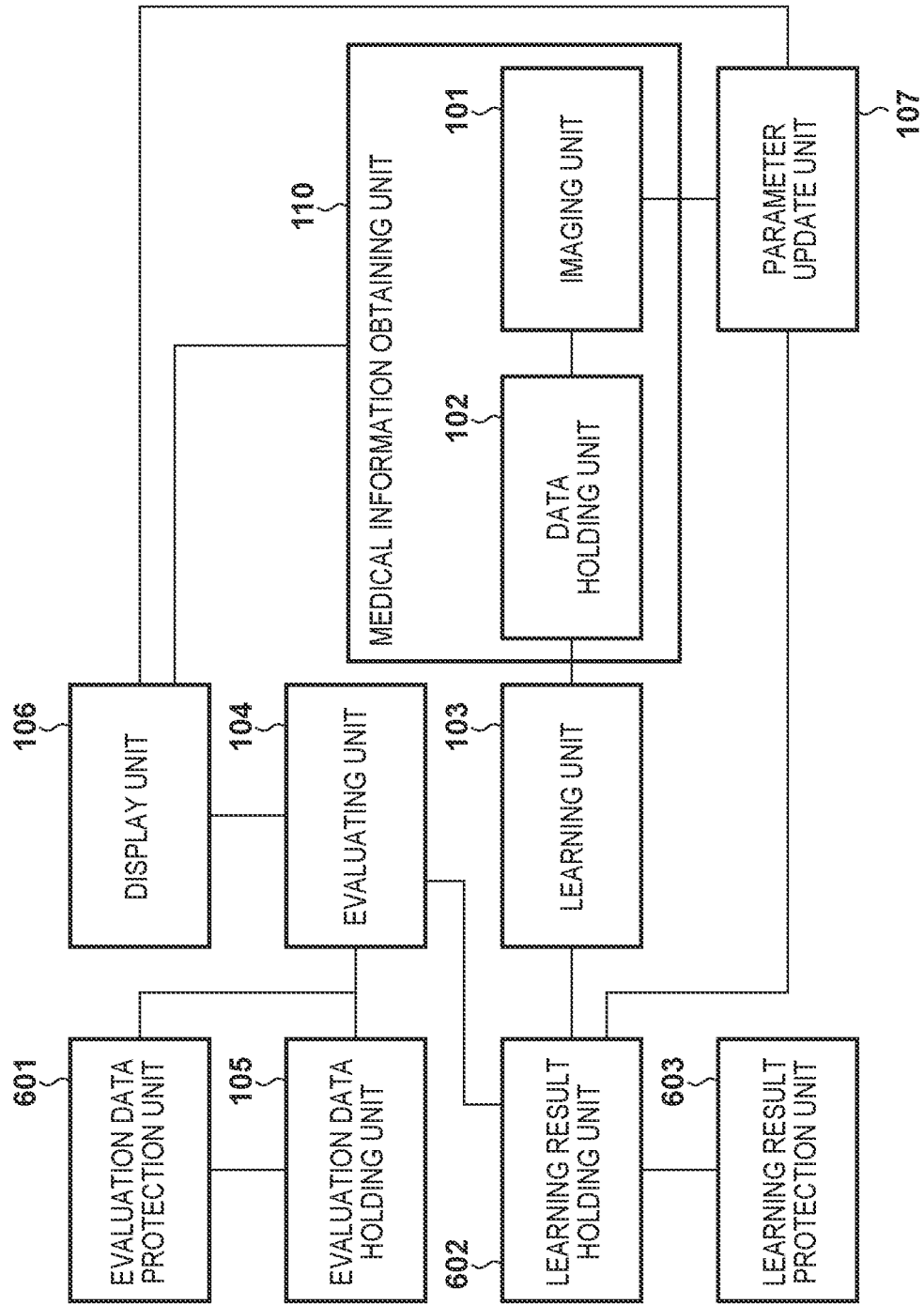
FIG. 6 is a diagram showing an exemplary function configuration of a medical information processing apparatus according to Modification 1.

FIG. 6 shows an exemplary function configuration of a medical information processing apparatus according to Modification 1. As shown in FIG. 6, the medical information processing apparatus 100 according to Modification 1 includes an evaluation data protection unit 601, a learning result holding unit 602, and a learning result protection unit 603 in addition to the above-described constituent elements of the first embodiment (FIG. 1). The evaluation data protection unit 601 protects evaluation data held in the evaluation data holding unit 105. The learning result holding unit 602 holds a learning result of the learning unit 103. The learning result protection unit 603 protects the learning result held in the learning result holding unit 602. Note that the hardware configuration of the medical information processing apparatus according to Modification 1 is similar to that in the first embodiment (FIG. 15). The evaluation data protection unit 601 detects that the evaluation data held in the evaluation data holding unit 105 has not been changed or erased. According to Modification 1, the evaluation data protection unit 601 confirms evaluation data before the evaluating unit 104 performs evaluation. The evaluation data protection unit 601 can detect the validity of the evaluation data by confirming the consistency through digital signature or hashing.

In addition, the evaluation data protection unit 601 may periodically back up evaluation data held in the evaluation data holding unit 105. Even if evaluation data held in the evaluation data holding unit 105 has been changed or erased, the evaluation data protection unit 601 can restore evaluation data before being changed or erased, by reading out the backed-up evaluation data.

The learning result holding unit 602 holds a result of learning performed by the learning unit 103. The evaluating unit 104 and the parameter update unit 107 perform individual processing using the learning result held in the learning result holding unit 602. The learning result protection unit 603 protects the learning result of the learning unit 103 held in the learning result holding unit 602. Accordingly, the learning result protection unit 603 detects that the learning result held in the learning result holding unit 602 has not been changed or erased. In Modification 1, the learning result is confirmed before it is set in the imaging unit 101. The learning result protection unit 603 can detect the validity of the learning result by confirming the consistency through digital signature or hashing, similarly to the evaluation data protection unit 601. In addition, the learning result protection unit 603 may also periodically back up the learning result held in the learning result holding unit 602 similarly to the evaluation data holding unit 105.

As described above, according to Modification 1, as a result of the evaluation data protection unit 601 protecting evaluation data, it is possible to prevent deterioration in the reliability of the evaluation data due to tampering, malfunction of the medical information processing apparatus, system trouble during update, and the like. In addition, a result of learning performed by the learning unit 103 is protected by the learning result protection unit 603, and thus deterioration in the reliability of learned parameters to be used by the evaluating unit 104 and the processing apparatus 42 is prevented.

Modification 2

According to the first embodiment, evaluation data is constituted by image data and irradiation field information, but, as described above, the present invention is also applicable to a medical information processing apparatus that uses other information. In Modification 2, an example will be described in which, when the same image data is associated with a plurality of pieces of information, attachment information of evaluation data indicates which piece of information the image data is associated with.

FIGS. 7A and 7B are diagrams showing examples of the correspondence relation between evaluation data held in the evaluation data holding unit 105 and learning results. As shown in FIG. 7A, evaluation data includes information regarding function types (image recognition, image processing, and photographic failure recognition), which are learning targets and information regarding imaging parts (a chest, abdomen, and a head) as attachment information, in addition to a medical image (image data) and correct-answer data. Accordingly, the evaluation data holding unit 105 holds attachment information indicating the correspondence relation between evaluation data and functions and/or attachment information indicating the correspondence relation between evaluation data and imaging parts. Accordingly, the evaluating unit 104 can read out, from the evaluation data holding unit 105, evaluation data corresponding to a function that is a learning target of the learning unit 103, based on attachment information, and perform evaluation.

In FIG. 7A, evaluation data 1 to 7 represent evaluation data held in the evaluation data holding unit 105. The evaluation data 1 includes a medical image of a chest and a correct result (correct-answer data) for when image recognition is performed on the medical image. The evaluation data 2 includes a medical image of a chest and correct-answer data for when image processing is performed on the medical image. The evaluation data 3 includes a medical image of an abdomen and correct-answer data for when photographic failure recognition is performed on the medical image. The evaluation data 4 includes a medical image of an abdomen and correct-answer data for when each of image recognition and image processing is performed on the medical image. The evaluation data 5 includes a medical image of a chest and correct-answer data for when each of image recognition and photographic failure recognition is performed on the medical image. The evaluation data 6 includes a medical image of a head and correct-answer data for when each of image recognition and image processing is performed on the medical image. The evaluation data 7 includes a medical image of a chest and correct-answer data when each of image recognition, image processing, and photographic failure recognition is performed on the medical image.

The same image data can be used for a plurality of purposes by tagging for indicating which information is attached to each piece of image data of evaluation data in this manner. As a result, it is possible to reduce an increase in the size of the system due to an increase in the data volume in the evaluation data holding unit 105.

The evaluating unit 104 associates a learning result of learning performed by the learning unit 103 with evaluation data held in the evaluation data holding unit 105. As shown in FIG. 7B, the learning result includes information regarding learning functions for which learning was performed by the learning unit 103 and imaging parts. A learning result 1 is a result of learning for image recognition of a medical image of a chest, and the evaluation data 1, the evaluation data 5, and the evaluation data 7, in which the type of function is image recognition and the imaging part is a chest, are extracted as evaluation data for the learning result 1 from the evaluation data holding unit 105. The extracted evaluation data 1, evaluation data 5, and evaluation data 7 are associated with the learning result 1, in addition, a learning result 2 is a result of learning for image processing of a medical image of an abdomen, and the evaluation data 4 in which the type of function is image processing and the imaging part is an abdomen is extracted from the evaluation data holding unit 105, and is associated with the learning result 2.

A learning result 3 is a result of learning for photographic failure recognition in a medical image of a head. The evaluation data holding unit 105 stores evaluation data in which the type of function is photographic failure recognition, but does not store evaluation data in which the imaging part is a head. If there is no corresponding evaluation data in this manner, the evaluating unit 104 according to Modification 2 extracts evaluation data based on the type of function, depending on the function, even if the imaging part is different between the evaluation data and the learning result. As a result, the evaluation data 3, the evaluation data 5, and the evaluation data 7 in which the type of function is photographic failure recognition are extracted, and are associated with the learning result 3.

A learning result 4 is a result for learning for operation recognition in a medical image of a chest. The evaluation data holding unit 105 does not hold evaluation data for which the type of function is operation recognition. In this case, the evaluating unit 104 recognizes that the evaluation data holding unit 105 does not store evaluation data that includes the learning function of operation recognition, and transmits, to the display unit 106, a message that the learning result 4 cannot be evaluated. As a result, the user can be aware that the learning result 4 cannot be evaluated. Note that, in this manner, a configuration may be adopted in which, if the evaluation data holding unit 105 does not hold evaluation data corresponding to operation recognition, the evaluating unit 104 requests an external apparatus (not illustrated) for evaluation data for operation recognition and obtains the evaluation data.

In addition, in Modification 2, an example has been described in which tables are prepared separately as shown in FIGS. 7A and 7B, but similar information may be included in tag information or the like that is recorded along with image data of evaluation data, in that case, evaluation data to be used for evaluating a learning result is selected by referencing the tag information of each medical image, instead of tables, in addition, information regarding a storage location of attached information, obtaining time and date, and the like can also be included in the tag of a medical image. As described above, according to Modification 2, it is possible to reduce an increase in the size of the system due to an increase in the data volume.

Second Embodiment

In a second embodiment, a description will be given on a system for updating evaluation data when more effective evaluation data for validity examination is obtained or a medical information processing apparatus is updated. In the second embodiment, creation and delivery of evaluation data different from the first embodiment will be described.

Figure 8:
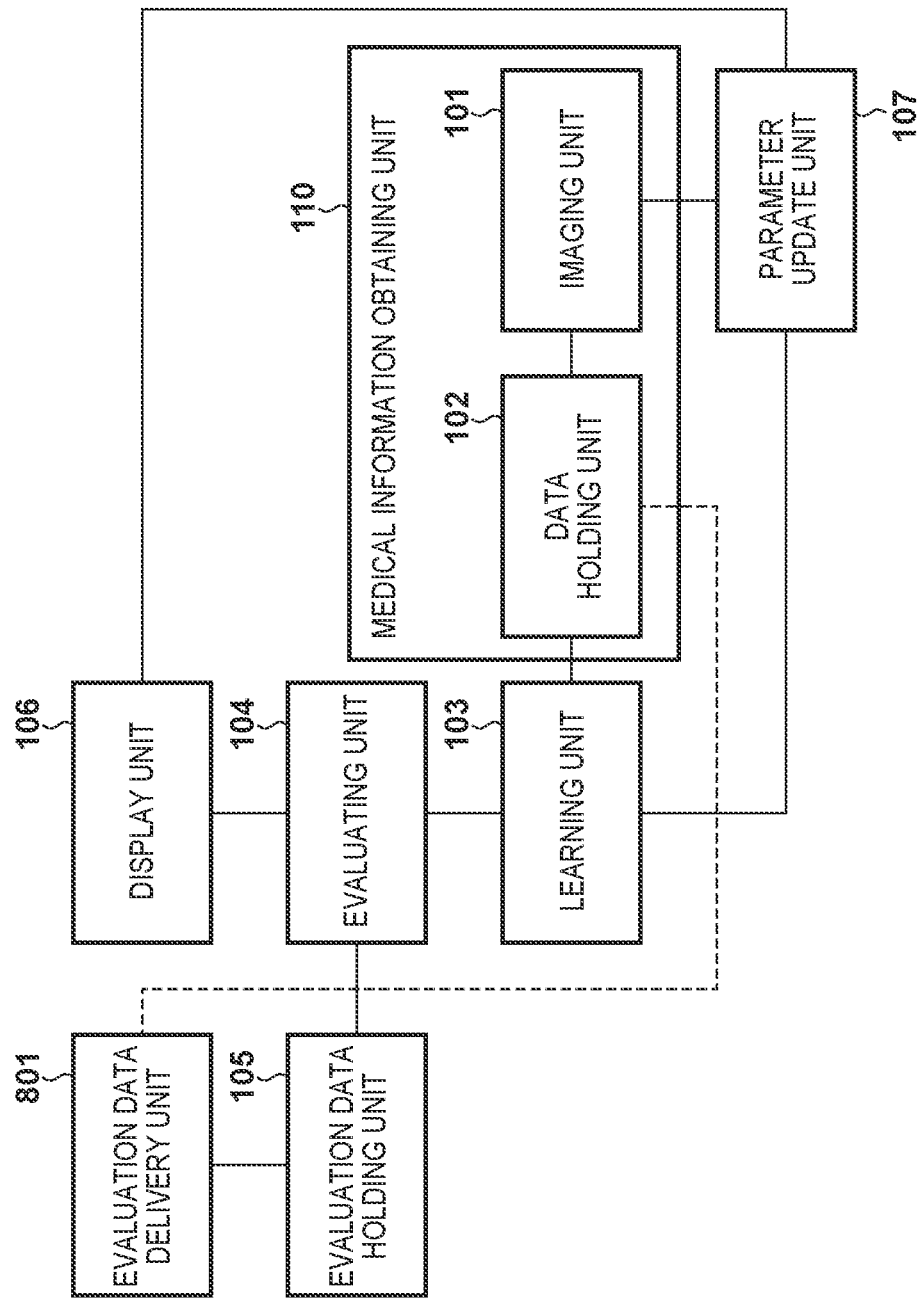
FIG. 8 is a diagram showing an exemplary function configuration of a medical information processing apparatus according to a second embodiment.

First, the configuration of the medical information processing apparatus 100 will be described with reference to FIG. 8. In FIG. 8, the same reference numerals are assigned to constitutes elements similar to the first embodiment (FIG. 1). As shown in FIG. 8, the medical information processing apparatus 100 according to the second embodiment includes an evaluation data delivery unit 801 in addition to the constituent elements of the first embodiment. The evaluation data delivery unit 801 delivers evaluation data for updating evaluation data held in the evaluation data holding unit 105. The evaluation data holding unit 105 updates the held evaluation data using the delivered evaluation data.

Note that the hardware configuration of a medical information processing apparatus according to the second embodiment is similar to the first embodiment (FIG. 15). Note that the evaluation data delivery unit 801 is realized as a cloud system. Therefore, the evaluation data delivery unit 801 connects evaluation data holding units 105 in a plurality of facility (a plurality of medical information processing apparatuses 100) via a network. Note that, in FIG. 8, the connection between the evaluation data delivery unit 801 and the data holding unit 102 (indicated by a broken line) is a configuration used in Modification 4, which may be omitted in the second embodiment.

Next, operations of the above-described medical information processing apparatus 100 will be described with reference to FIG. 9. FIG. 9 is a flowchart illustrating operations of the medical information processing apparatus 100 according to the second embodiment. In FIG. 9, the same step numbers are assigned to steps for performing processes similar to the first embodiment (FIG. 2). In step S901, the evaluation data delivery unit 801 delivers evaluation data to the evaluation data holding unit 105. Accordingly, evaluation data held in the evaluation data holding unit 105 is updated. Note that it is conceivable that this update is performed when the imaging unit 101 of the medical information processing apparatus 100 is changed, this update is performed periodically, for example, every month, or this update is performed at any timing instructed by the user or distributer. In step S204, the evaluating unit 104 evaluates the result of learning performed by the learning unit 103, using the updated evaluation data held in the evaluation data holding unit 105.

Figure 10A:
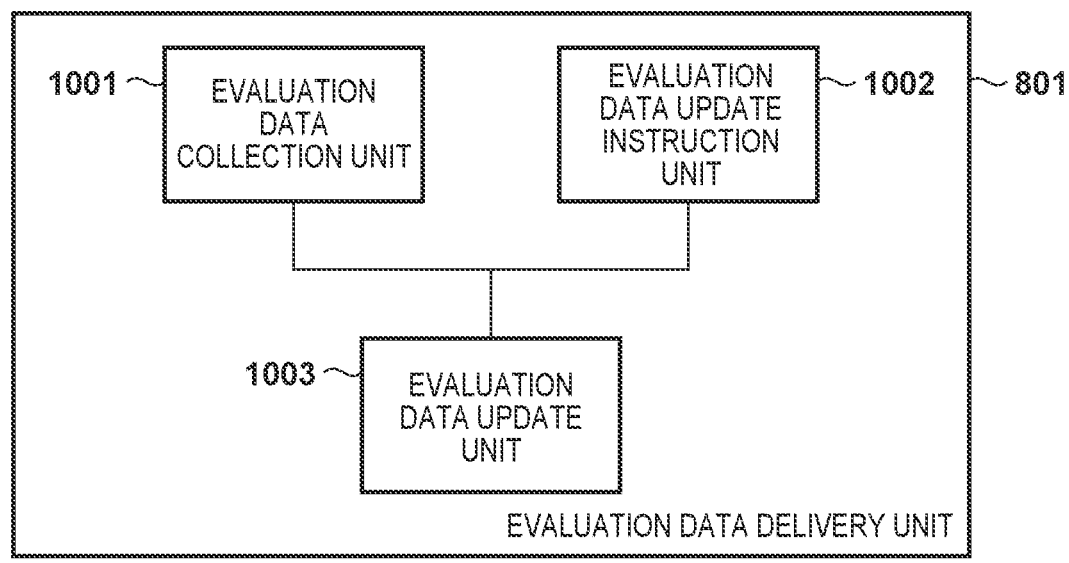
FIG. 10A is a diagram showing an exemplary function configuration of an evaluation data delivery unit according to the second embodiment.
Figure 10B:
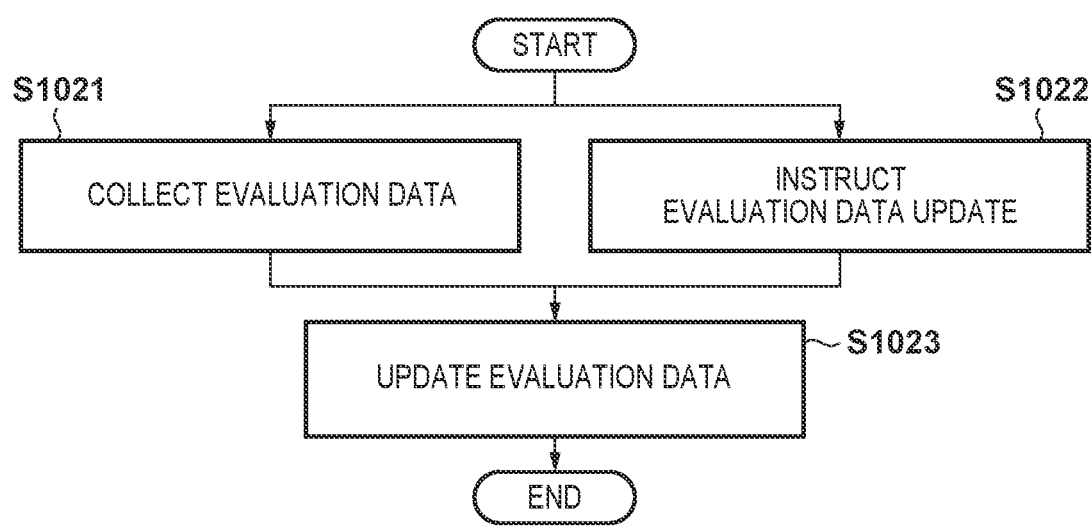
FIG. 10B is a flowchart showing the processing procedure of the evaluation data delivery unit according to the second embodiment.

Next, processing of the evaluation data delivery unit 801 will be described in detail with reference to FIGS. 10A and 10B. FIG. 10A is a block diagram showing an exemplary function configuration of the evaluation data delivery unit 801. The evaluation data delivery unit 801 includes an evaluation data collection unit 1001, an evaluation data update instruction unit 1002, and an evaluation data update unit 1003. Operations of the evaluation data delivery unit 801 that has above-described configuration will be described with reference to the flowchart in FIG. 10B.

In step S1021, the evaluation data collection unit 1001 collects evaluation data. Evaluation data can be collected from image data in a plurality of facilities or the like by a cloud system. In addition, a dataset for machine learning publicized on the Internet called a "public dataset" can also be used as evaluation data. According to this embodiment, evaluation data is image data obtained through radiography and irradiation field information, similarly to the first embodiment.

In step S1022, the evaluation data update instruction unit 1002 outputs an update instruction instructing that update be executed using the evaluation data collected by the evaluation data collection unit 1001. The content of the update instruction includes a target facility, update time and date, the type of delivery data, the number of pieces of delivery data, change and correction of evaluation data in the evaluation data holding unit 105, a target function, and the like. In step S1023, the evaluation data update unit 1003 updates the evaluation data held in the evaluation data holding unit 105, based on the instruction from the evaluation data update instruction unit 1002.

As described above, it is possible to update evaluation data held in the evaluation data holding unit 105 by performing the processes in steps S1021 to S1023. As a result, even if performance of the medical information processing apparatus 100 changes, it is possible to perform administration such that performance required for a clinical practice is satisfied. As a result of delivering evaluation data in this manner, even when the image capturing method that uses the medical information processing apparatus, parameters, or the like is changed, the user can easily perform validity examination by updating the evaluation data. In addition, according to the second embodiment, also when a new evaluation policy is used as evaluation data, or evaluation is performed on anew function, content held in the evaluation data holding unit 105 can be updated to effective evaluation data.

Modification 3

According to Modification 3, the evaluation data update instruction unit 1002 determines update content depending on the type of facility in which the medical information processing apparatus 100 is installed, the type of area, and the type of imaging system of the medical information processing apparatus 100 (function to be used).

Classification according to the number of hospital beds, classification of clinical departments, and the like are conceivable as examples of the type of facility. For example, in a case of a clinic with a small number of hospital beds, chests and abdomens are captured in large numbers as radiation images, and thus evaluation data held in the evaluation data holding unit 105 may be updated such that the ratio of evaluation data of chests and abdomens is high. Also, in the case of a hospital with a large number of hospital beds, imaging before and after surgery is performed in large numbers, and thus data may be updated such that the data ratio of patients is high. In an orthopedic hospital, shoulders, waists, hip joints, knees, and the like are captured in large numbers, and thus the evaluation data holding unit 105 may be updated such that the ratio of evaluation data of such images is high. In a hospital specialized for children, newborn infants and children are captured in most cases, and thus the evaluation data holding unit 105 may be updated such that the data ratio of such images is high.

In addition, classification of countries, cities, and rural areas, and the like are conceivable as examples of the type of area. In the case of a radiation image, imaging technique and technique may be different depending on countries, and thus a case is conceivable in which data captured in another country is not suitable for validity examination. In such a case, it is desirable to update evaluation data using data collected in the country. In addition, age distribution, body shapes, and the like may be different according to a city or rural area, and thus it is conceivable to update evaluation data based on statistical information such as distribution of ages or body shapes, or the like in the area.

In addition, update content may be determined according to the type of detector of the imaging system, the type of image processing algorithm, or the like as the type of imaging system. Classification according to a fluorescent material mounted in a detector, a pixel pitch, noise characteristics, sharpness characteristics, sensitivity, linearity, or the like is conceivable as the type of detector of a radiation image imaging system. For example, in indirect Flat Panel Detectors that are used as a radiation image imaging system, GOS, CsI, and the like are used as fluorescent materials fix converting radiation into visible light, and the film thicknesses thereof vary. Sensitivity, sharpness, and the like are different according to a fluorescent material, and thus, it is desirable to update evaluation data using data obtained by/in a system similar to the imaging system used in the facility that is a data update target. In addition, the difference between Computed Radiography system and Digital Radiography system, the type of the manufacturer that manufactured the detector, or the like is conceivable as the type of detector.

In addition, different algorithms of tone processing, the presence or absence of an image processing function for improving the image quality such as scattering radiation reducing processing or the like, or classification according to parameter intensity or the like is conceivable as the type of image processing algorithm. For example, the contrast of an image differs according to the presence or absence of scattering radiation reducing processing for reducing components of scattering radiation generated from an irradiated subject. Therefore, it is desirable to determine update content of evaluation data depending on whether or not the facility is using the scattering radiation reducing processing function (function to be used).

As described above, as a result of determining the content of an instruction of update data depending on the type of facility, the type of area, the type of imaging system (function to be used), or the like, it is possible to accurately evaluate performance required for a clinical practice.

In addition, in Modification 3, the radiation image imaging system has been described as an example of the type of medical information processing apparatus, but there is no limitation thereto. The medical information processing apparatus can be applied to any apparatuses such as CT apparatuses, MRI apparatuses, ultra-sonic apparatuses, fundus camera apparatuses, OCT apparatuses, endoscopes, and the like. For example, it is conceivable that, regarding a CT apparatus, update data is determined based on the number of rows of detectors or the type of reconfiguration algorithm, and, regarding an MRI apparatus, update data is determined based on the magnetic field intensity or the like.

Modification 4

According to above Modification 3, the evaluation data update instruction unit 1002 determines update content based on the type of facility, an area, the type of imaging system, or a function to be used. In Modification 4, a method for determining update content based on data obtained by the medical information obtaining unit 110 will be described.

Figure 11A:
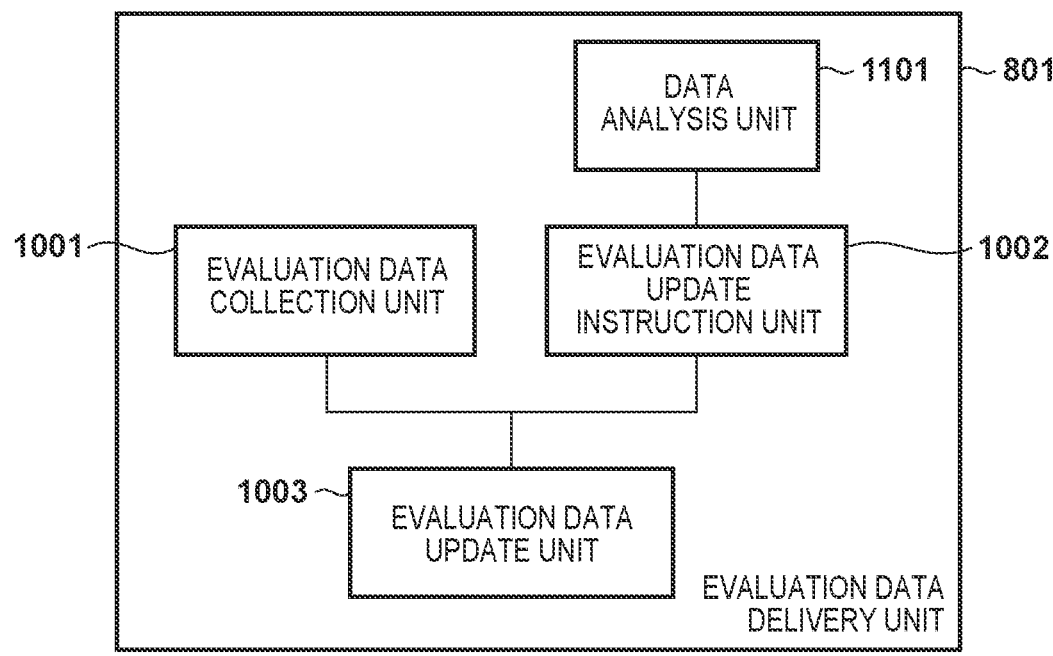
FIG. 11A is a diagram showing an exemplary function configuration of an evaluation data delivery unit according to Modification 4.

In the configuration of the medical information processing apparatus 100 according to Modification 4, in the configuration shown in the second embodiment (FIG. 8), the evaluation data delivery unit 801 and the data holding unit 102 are connected (indicated by broken like in FIG. 8). FIG. 11A is a diagram showing an exemplary function configuration of the evaluation data delivery unit 801 according to Modification 4. A data analysis unit 1101 is provided in addition to the configuration of the second embodiment (FIG. 10A). The data analysis unit 1101 is connected to the evaluation data update instruction unit 1002. In this configuration, the data holding unit 102 holds image data obtained by the imaging unit 101 and a processing result obtained as a result of applying a function to the image data. The evaluation data delivery unit 801 selects evaluation data for updating the evaluation data holding unit 105, based on the result of analyzing the image data held in the data holding unit 102, and delivers the selected data.

Figure 11B:
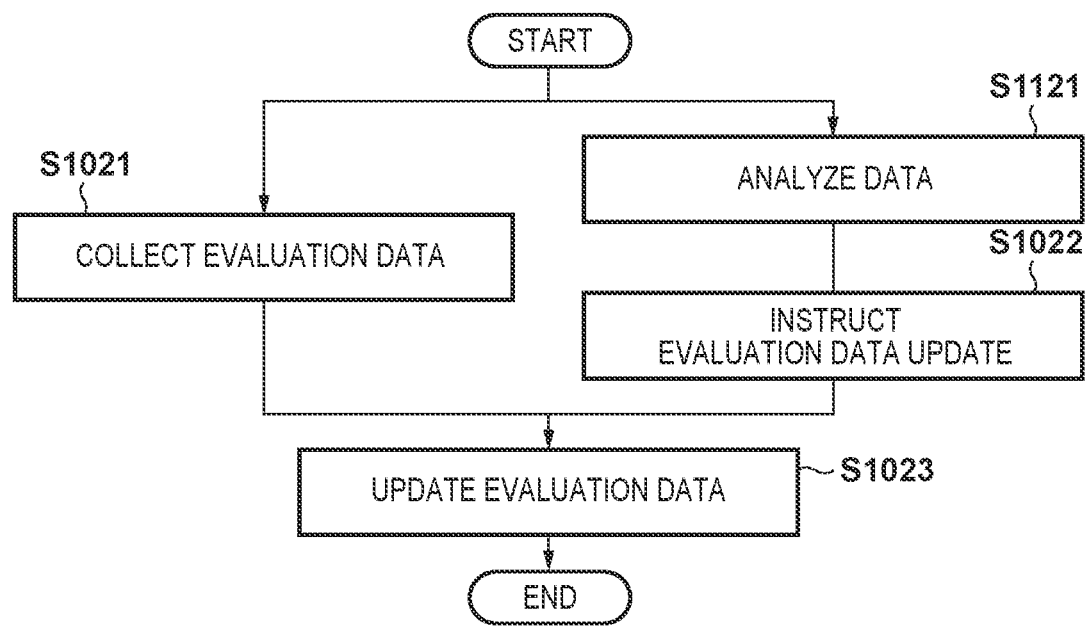
FIG. 11B is a flowchart showing the processing procedure of the evaluation data delivery unit according to Modification 4.

Next, operations of the evaluation data delivery unit 801 according to Modification 4 will be described with reference to FIG. 11B. In step S1021, the evaluation data collection unit 1001 collects evaluation data. The detailed step S1021 is similar to the second embodiment (step S1021 in FIG. 10B). In step S1121, the data analysis unit 1101 analyzes data held in the data holding unit 102. Examples of analysis content include "imaging condition", "image processing condition", "the ratio of the number of pieces of captured image data", "age", "gender", and "body shape".

In the case of imaging of an X-ray image, for example, a tube voltage and tube current when captured image data is obtained, an imaging time, the distance between an X-ray generation apparatus and a sensor, the presence or absence of a scattered radiation removing grid, or the type of sensor can be used as the "imaging condition". Parameters for tone processing, sharpness emphasis, and noise suppression, and the like can be used as the "image processing condition". The ratio of the number of pieces of data for each type of captured image such as chest imaging, abdomen imaging, shoulder joint imaging, or lumbar spine imaging can be used as "the ratio of the number of pieces of captured image data". In addition, the ratio of the number of pieces of data for each of age, gender, and body shape may also be used as "the ratio of the number of pieces of captured image data". The data analysis unit 1101 performs above-described analysis by analyzing image data stored in the data holding unit 102 and information stored along with the image data.

Next, in step S1022, the evaluation data update instruction unit 1002 instructs that evaluation data be updated based on the result of data analysis performed by the data analysis unit 1101. For example, assume that an analysis result in which chest imaging is 60%, abdomen imaging is 30%, and lumbar spine imaging is 10% was obtained by the data analysis unit 1101. In this case, the evaluation data update instruction unit 1002 instructs that evaluation data be updated such that the ratio of chest image data is 60%, the ratio of abdomen image data is 30%, and the ratio of lumbar spine image data is 10%. Note that, according to Modification 4, the ratios in an analysis result and the ratios in an update instruction are the same, but there is no limitation thereto. For example, the evaluation data update instruction unit 1002 may determine the ratios based on an analysis result. For example, an update instruction may be prepared using both the content of the last update instruction and an analysis result (for example, using the average value of them). In step S1023, the evaluation data is updated in accordance with an evaluation data update instruction. Step S1023 is similar to the second embodiment (step S1023 in FIG. 10B).

As a result of performing the above processes in steps S1021 to S1023, the evaluation data can be updated. In this manner, it is possible to analyze data held in the data holding unit 102 for each medical information obtaining unit 110, and update the data to evaluation data suitable for the medical information obtaining unit 110. Accordingly, even if performance changes due to machine learning, it is possible to accurately evaluate performance required for a clinical practice.

In the above second embodiment and Modifications 3 and 4, examples have been described in which the evaluation data delivery unit 801 that selects data for updating evaluation data, and provides the data to the evaluation data holding unit 105 is provided on a cloud, but there is no limitation thereto. For example, the evaluation data delivery unit 801 may also be provided in the information processing apparatus 10. For example, a configuration may also be adopted in which data to be used for the evaluation data delivery unit 801 of the information processing apparatus 10 to update evaluation data is selected from evaluation data provided by a USB memory, a storage apparatus on the network, or the like, and the evaluation data is updated by the evaluation data holding unit 105.

Third Embodiment

According to the second embodiment, evaluation data for updating the evaluation data holding unit 105 is obtained from outside. In the third embodiment, a description will be given on the medical information processing apparatus 100 that uses a portion of data obtained by the medical information obtaining unit 110 as evaluation data for validity examination, and uses another portion as learning data. The configuration of the medical information processing apparatus 100 according to the third embodiment will be described with reference to FIG. 12. FIG. 12 is a block diagram showing an exemplary function configuration of the medical information processing apparatus 100 according to the third embodiment. An exemplary hardware configuration of the medical information processing apparatus 100 is similar to the first embodiment (FIG. 15). In FIG. 12, the same reference numerals are assigned to constituent elements similar to the first embodiment (FIG. 1).

The medical information processing apparatus 100 according to the third embodiment includes a data designation unit 1201 and a learning data holding unit 1202 in addition to the constituent elements of the first embodiment (FIG. 1). The data designation unit 1201 is connected to the data holding unit 102, the evaluation data holding unit 105, and the learning data holding unit 1202. The data designation unit 1201 designates data used for updating evaluation data and data used as learning data, from data held in the data holding unit 102, and updates the data. Specifically, the data designation unit 1201 updates evaluation data held in the evaluation data holding unit 105, such that at least a portion of image data held in the data holding unit 102 is set as evaluation data. In addition, the data designation unit 1201 updates learning data held in the learning data holding unit 1202, such that at least a portion of image data held in the data holding unit 102 is set as learning data.

Figure 13:
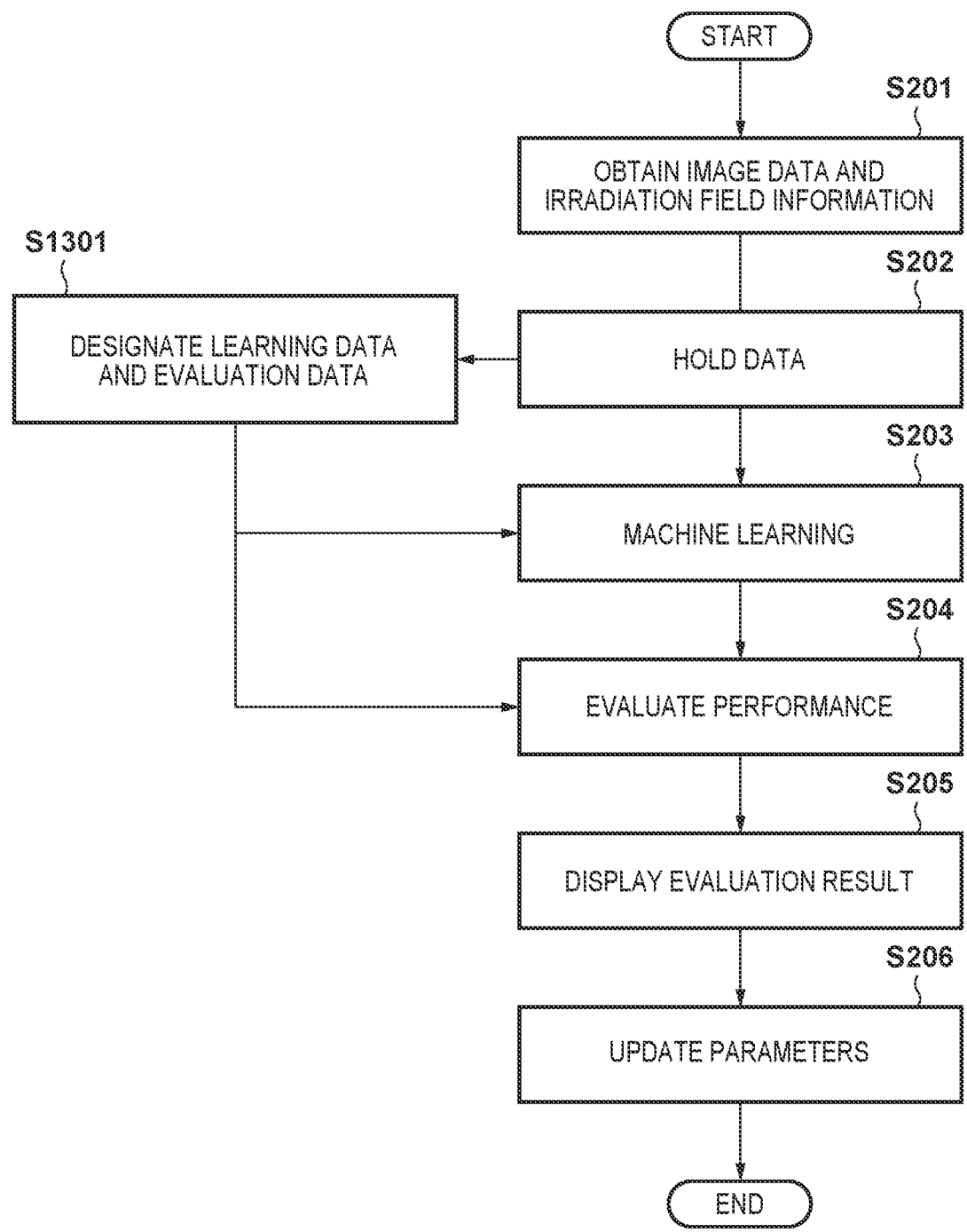
FIG. 13 is a flowchart showing the processing procedure of the medical information processing apparatus according to the third embodiment.

Next, operations of the medical information processing apparatus 100 according to the third embodiment will be described with reference to FIG. 13. In FIG. 13, the same step numbers are assigned to processes similar to the first embodiment (FIG. 2). First, in step S201, the imaging unit 101 obtains a radiation image of a subject and irradiation field information. In step S202, the data holding unit 102 holds the radiation image and irradiation field information obtained by the imaging unit 101. In step S1301, the data designation unit 1201 reads out data held in the data holding unit 102, and designates the data as evaluation data or learning data. The data designated as evaluation data is output to the evaluation data holding unit 105, and the data designated as learning data is output to the learning data holding unit 1202. In this manner, the evaluation data and the learning data are updated. A data designation method that is performed by the data designation unit 1201 will be described in detail later.

In step S203, the learning unit 103 performs machine learning using the data designated as learning data in the learning data holding unit 1202, and obtains a learning result. In step S204, the evaluating unit 104 performs performance evaluation of the learning result output by the learning unit 103, using the evaluation data held in the evaluation data holding unit 105, and outputs an evaluation result. In step S205, the display unit 106 displays the evaluation result output by the evaluating unit 104. In step S206, if it is determined that the learning result is valid, based on the evaluation result, the parameter update unit 107 updates parameters of the irradiation field recognition function of the imaging unit 101. As a result of performing the processes of steps S201 to S206, and S1301 in this manner, validity examination of machine learning can be performed.

According to the third embodiment, by using, for validity examination, data obtained by the medical information obtaining unit 110 that is a learning target, it is possible to more accurately measure performance required for a clinical practice. By using a method for updating evaluation data according to the third embodiment, even if there are a plurality of medical information obtaining units 110 that have different tendencies according to each facility such as imaging condition and imaging method, the evaluation data holding unit 105 can hold evaluation data appropriate for each of the medical information obtaining units 110. In addition, if all of the constituent elements of the medical information processing apparatus 100 are in the same facility, even when there is no communication environment of the Internet, the validity examination can be performed after the performance is changed.

Figure 14A:
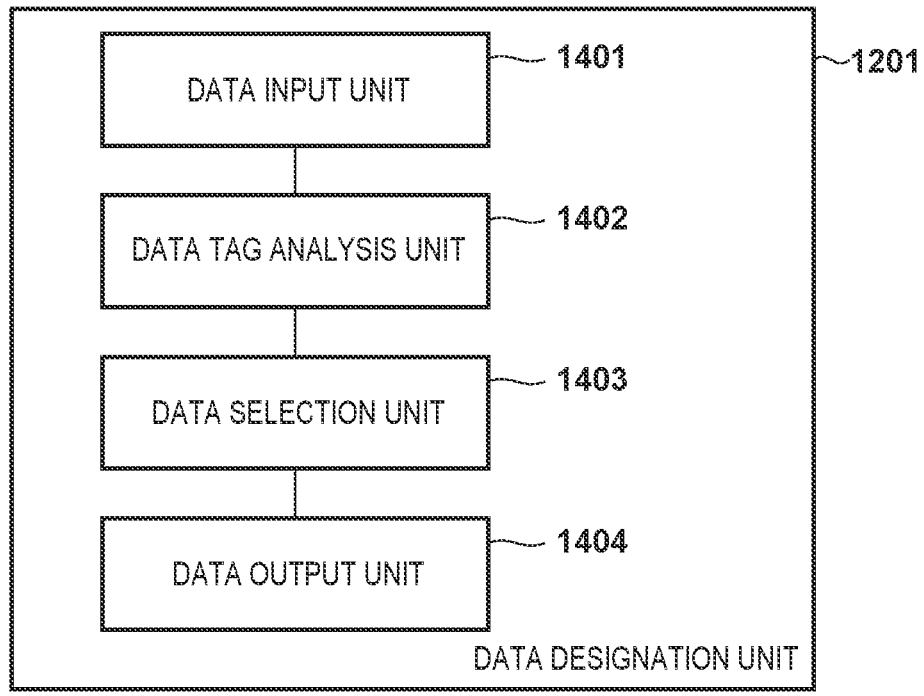
FIG. 14A is a diagram showing an exemplary function configuration of a data designation unit according to the third embodiment.
Figure 14B:
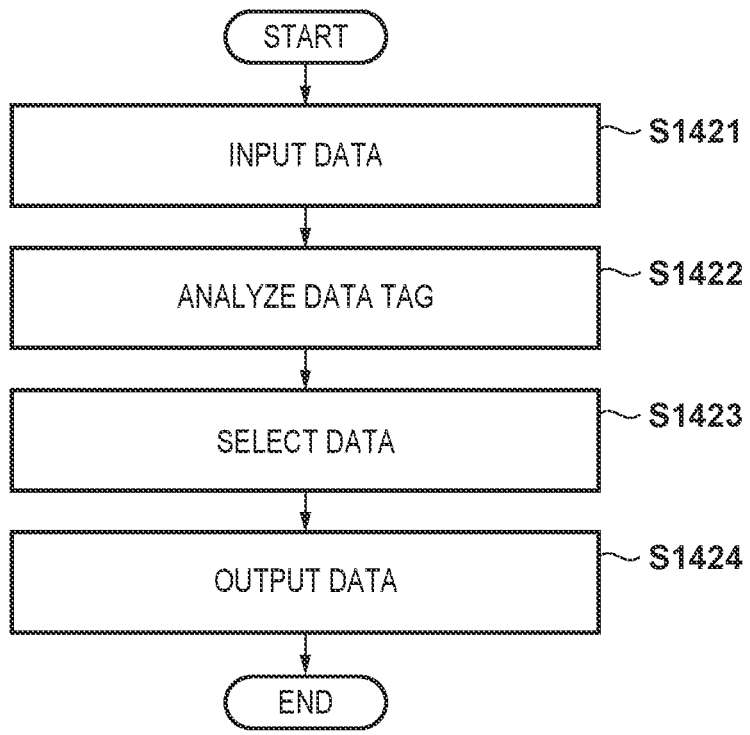
FIG. 14B is a flowchart showing the processing procedure of the data designation unit according to the third embodiment.

Next, the above-described data designation method that is performed by the data designation unit 1201 will be described in detail with reference to FIGS. 14A and 14B. FIG. 14A is a block diagram showing an exemplary function configuration of the data designation unit 1201. As shown in FIG. 14A, the data designation unit 1201 includes a data input unit 1401, a data tag analysis unit 1402, a data selection unit 1403, and a data output unit 1404. FIG. 14B is a flowchart illustrating operations of the data designation unit 1201.

In step S1421, image data and irradiation field information are input from the data holding unit 102 to the data input unit 1401. Note that data tags of imaging condition, imaging part, photographer, imaging location, imaging time and date, and the like are attached to the image data as attached information. Next, in step S1422, the data tag analysis unit 1402 analyzes the attached information of the image data input to the data input unit 1401. According to this embodiment, analysis is performed on whether or not the photographer of the image data is a designated user, or the like. Next, in step S1423, the data selection unit 1403 makes a selection to set the image data as evaluation data or learning data, based on the analysis result of the data tag analysis unit 1402. According to this embodiment, if the photographer of the image data is a designated user, the image data is set as evaluation data, otherwise the image data is set as learning data. With such a configuration, it is possible to set accurate data captured by a trusted user, as evaluation data. Next, in step S1424, the data output unit 1404 outputs data to the evaluation data holding unit 105 or the learning data holding unit 1202, based on the result of the selection made by the data selection unit 1403.

As described above, as a result of performing the processes of steps S1421 to S1424, the data designation unit 1201 can designate data. By setting image data as evaluation data or learning data according to the type of the image data in this manner, it is possible to select data suitable for validity examination.

Note that, according to this third embodiment, a determination is made on whether image data is to be used as evaluation data or learning data, based on whether or not the photographer of the image data is a designated user, but there is no limitation thereto as a matter of course. For example, such a determination may also be made based on whether or not the imaging time is in the morning, whether the imaging place is a patient's hospital room, an operation room, or an imaging room, whether the imaging part is a chest, an abdomen, or bones, or the like, or a combination of some of those may also be used. For example, as a result of selecting data to be used as evaluation data, from the data holding unit 102 according to the imaging frequency of an imaging part, performance evaluation can be performed in a form close to an actual operating situation. For example, when the imaging frequency of a chest is 70%, the imaging frequency of an abdomen is 20%, and the imaging frequency of bones is 10%, data of the imaging parts may be selected such that evaluation data has those ratios.

In addition, according to the third embodiment, it is not necessary to use all the data in the data holding unit 102, and a portion of the data may be allocated as each of evaluation data and learning data. In this case, the data designation unit 1201 designates three types of data, namely evaluation data, learning data, and data that is not used for evaluation nor learning. With such a configuration, it is possible to adjust the system load for evaluation and learning.

Modification 5

According to the third embodiment, a selection is made whether image data is to be used as evaluation data or learning data, by analyzing data tag (attached information) of the image data. According to Modification 5, evaluation data or learning data is generated by changing image data obtained by the data holding unit 102. Although not illustrated, a data charge unit that changes image data as described above is provided in place of the data tag analysis unit 1402. Examples of a change in image data include tone processing (noise superimposition, luminance change, and contrast change), rotation, translation, deformation, enlargement, and reduction. The data selection unit 1403 designates a pair of changed image data and a processing result or a pair of image data before being changed and the processing result, as evaluation data to be used by the evaluating unit 104, and designates the other pair as learning data to be used by the learning unit 103. Here, the processing result is a result of executing processing on image data before being changed, based on a function of the processing apparatus 42. For example, the data selection unit 1403 designates data changed by the data change unit and a processing result as learning data, and designates unchanged data (the data before being changed) and the processing result as evaluation data. In this case, it is possible to increase the number of pieces of learning data, and set data to be used for medical examination, as evaluation data. In addition, the data selection unit 1403 may select data before being changed by the data change unit and a processing result as learning data, and select changed data and at least a portion of the processing result as evaluation data. In such a case, evaluation data can be increased.

Modification 6

According to the third embodiment, data is selected as evaluation data or learning data by performing data tag analysis, and according to Modification 5, data is selected as evaluation data or learning data based on whether or not the image data has been changed. According to Modification 6, the user directly selects evaluation data using a selection screen. The display unit 106 displays, on the selection screen, image data, irradiation field information, attached information, and the like held in the data holding unit 102, and the user references the displayed data and information, and designates the image data that is being displayed is to be used as evaluation data or learning data. With such a configuration, the user can select image suitable for performance evaluation as evaluation data, and it is possible to make it easy to perform validity determination.

Modification 7

According to the third embodiment, data is selected as evaluation data or learning data by performing data tag analysis. According to Modification 7, data is selected as evaluation data or learning data as a result of analyzing image data itself. According to Modification 7, the data tag analysis unit 1402 in FIG. 14A is replaced with an image data analysis unit, which analyzes image data, and distinguishes between an image with a metal included in the image data thereof and an image without a metal. The data selection unit 1403 selects each piece of image data as evaluation data or learning data, based on the analysis result, in other words according to the presence or absence of a metal in the image.

Note that, in the above description, the presence or absence of a metal in an image is used as a criterion for selecting a usage, namely evaluation data or learning data, but there is no limitation thereto. For example, the index of noise in an image, the index of sharpness, or the index of body frame may also be used as a criterion for selecting a usage. In addition, it is also possible to select a usage based on irradiation field information. For example, data may be selected such that no bias is generated with respect to the angle between a radiation detector plane and an irradiation field, the size of irradiation field, the aspect ratio, and the shapes such as circle, rectangle, and polygon. In addition, the ratios of them may also be determined according to the ratios in image data captured by the imaging unit 101 of the medical information obtaining unit 110. With such a configuration, it is possible to reduce the number of cases where validity examination cannot be sufficiently performed due to biased distribution of evaluation data content.

Note that the configurations described in embodiments and Modification can be suitably combined and used.

According to the above-described embodiments, it is possible to examine the validity of machine learning in a medical information processing apparatus.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A medical information processing apparatus, comprising:
    at least one of (a) one or more processors connected to one or more memories storing a program including instructions executed by the one or more processors and (b) circuitry configured to perform:
    obtaining medical information;
    learning on a function of the medical information processing apparatus using the medical information, the learning being performed on any one of: image recognition including region information as a result obtained by processing using the function, image processing including image processing conditions as a result obtained by processing using the function, and diagnostic support including lesion position information in a processing result as a result obtained by processing using the function; and
    evaluating a learning result using a result obtained by comparing, for each corresponding pixel, (c) a result obtained by processing a medical image included in an evaluation data using the learning result, and (d) the correct answer data included in the evaluation data, wherein the learning result is obtained by learning related to any one of the image recognition and the image processing and the diagnostic support, wherein the evaluation data is for evaluating the learning result by the learning, wherein the evaluation data is included the medical image and the correct-answer data in which a correct answer for each of the image recognition, the image processing, and the diagnostic support is known, and wherein the evaluation data is selected in accordance with a type of the function.

2. The medical information processing apparatus according to claim 1, wherein the at least one of (a) one or more processors and (b) circuitry is configured to perform the function of reading evaluation data related to content of machine learning that is performed by the performing, from the evaluation data held in the holding, and evaluating a learning result.

3. The medical information processing apparatus according to claim 1, wherein the at least one of (a) one or more processors and (b) circuitry is further configured to perform the function of:
updating a parameter that is used for the function, based on evaluation of the learning result.

4. The medical information processing apparatus according to claim 3, wherein when a learning result obtained through machine learning performed by the performing improves, the at least one of (a) one or more processors and (b) circuitry is configured to perform the function of updating the parameter of the function.

5. The medical information processing apparatus according to claim 1, wherein the at least one of (a) one or more processors and (b) circuitry is further configured to perform the function of protecting the evaluation data held in the evaluating.

6. The medical information processing apparatus according to claim 1, wherein the at least one of (a) one or more processors and (b) circuitry is further configured to perform the function of:
holding a learning result of machine learning; and
protecting the learning result held in the learning.

7. The medical information processing apparatus according to claim 1, wherein the at least one of (a) one or more processors and (b) circuitry is configured to perform the function of:
holding the evaluation data according to an image-capturing mode; and
performing evaluation using evaluation data corresponding to an image-capturing mode of a function that is a learning target of machine learning.

8. The medical information processing apparatus according to claim 1, wherein the at least one of (a) one or more processors and (b) circuitry is configured to perform the function of:
holding attachment information indicating a correspondence relation between the evaluation data and the function; and
reading out, from the evaluation data holding unit, evaluation data corresponding to a function that is a learning target of machine learning, based on the attachment information, and performing the evaluation.

9. The medical information processing apparatus according to claim 8, wherein the attachment information further includes an imaging part.

10. The medical information processing apparatus according to claim 1, wherein the at least one of (a) one or more processors and (b) circuitry is further configured to perform the function of:
delivering evaluation data for updating evaluation data held in the holding; and
updating the evaluation data held in the holding, using the delivered evaluation data.

11. The medical information processing apparatus according to claim 10, wherein the at least one of (a) one or more processors and (b) circuitry is configured to perform the function of:
determining evaluation data to be delivered, based on at least one of a type of facility in which the medical information processing apparatus is installed, a type of area in which the medical information processing apparatus is installed, and a type of imaging system of the medical information processing apparatus.

12. The medical information processing apparatus according to claim 10, wherein the at least one of (a) one or more processors and (b) circuitry is further configured to function as:
holding image data obtained by imaging and a processing result obtained by applying the function to the image data,
wherein the at least one of (a) one or more processors and (b) circuitry is configured to function as selecting evaluation data for updating the evaluation data-holding unit, based on an analysis result of the image data held in the holding, and delivering the selected evaluation data.

13. The medical information processing apparatus according to claim 12,
wherein the analysis result includes, for the image data held in the holding, at least one of an imaging condition, an image processing condition, a ratio of a number of pieces of data classified by an imaging part, and a ratio of a number of pieces of data classified by an attribute of a subject.

14. The medical information processing apparatus according to claim 1, wherein the at least one of (a) one or more processors and (b) circuitry is configured to function as:
holding image data obtained by imaging and a processing result obtained by the function being applied to the image data; and
updating the evaluation data held in the holding such that at least a portion of the image data held in the holding is used as the evaluation data.

15. The medical information processing apparatus according to claim 14,
wherein the at least one of (a) one or more processors and (b) circuitry is configured to function as designating the image data and the processing result that are held in the holding, as being used as the evaluation data or learning data of machine learning, based on attached information attached to the image data.

16. The medical information processing apparatus according to claim 14, wherein the at least one of (a) one or more processors and (b) circuitry is further configured to function as
changing the image data held in the holding,
wherein the at least one of (a) one or more processors and (b) circuitry is configured to function as designating one of a pair of image data changed by the changing and a processing result and a pair of the image data before being changed and the processing result, as evaluation data to be used by the evaluating, and designating the other pair as learning data to be used by machine learning.

17. The medical information processing apparatus according to claim 1, wherein the correct answer data, included in the evaluation data for the image recognition, includes, as the region information, at least one of an irradiation field region, an anatomical region, and a lesion region.

18. The medical information processing apparatus according to claim 1, wherein the correct answer data, included in the evaluation data for the image processing, includes, as the image processing condition, at least one of a tone processing condition and a noise processing condition.

19. The medical information processing apparatus according to claim 1, wherein the at least one of (a) one or more processors and (b) circuitry is configured to function as:
evaluating the learning result using, as a result of comparing for each corresponding pixel, using a match rate obtained using a number of a pixel matched each other or a number of a pixel not matched each other.

20. A medical information processing method, comprising:
    obtaining medical information;
    learning on a function of a medical information processing apparatus using the medical information, the learning being performed on any one of image recognition including region information as a result obtained by processing using the function, image processing including image processing conditions as a result obtained by processing using the function, and diagnostic support including lesion position information in a processing result as a result obtained by processing using the function; and
    evaluating a learning result using a result obtained by comparing, for each corresponding pixel, (c) a result obtained by processing a medical image included in an evaluation data using the learning result, and (d) the correct answer data included in the evaluation data, wherein the learning result is obtained by learning related to any one of the image recognition and the image processing and the diagnostic support, wherein the evaluation data is for evaluating the learning result by the learning, wherein the evaluation data includes the medical image and the correct-answer data in which a correct answer for each of the image recognition, the image processing, and the diagnostic support is known, and wherein the evaluation data is selected in accordance with a type of the function.

21. A non-transitory computer-readable storage medium storing a program for causing a computer to execute a method comprising:
    obtaining medical information;
    learning on a function of a medical information processing apparatus using the medical information, the learning being performed on any one of: image recognition including region information as a result obtained by processing using the function, image processing including image processing conditions as a result obtained by processing using the function, and diagnostic support including lesion position information in a processing result as a result obtained by processing using the function; and
    evaluating a learning result using a result obtained by comparing, for each corresponding pixel, (c) a result obtained by processing a medical image included in an evaluation data using the learning result, and (d) the correct answer data included in the evaluation data, wherein the learning result is obtained by learning related to any one of the image recognition and the image processing and the diagnostic support, wherein the evaluation data is for evaluating the learning result by the learning, wherein the evaluation data is included the medical image and the correct-answer data in which a correct answer for each of the image recognition, the image processing, and the diagnostic support is known, and wherein the evaluation data is selected in accordance with a type of the function.

* * * * *